US008447413B2

(12) United States Patent
Stone et al.

(10) Patent No.: US 8,447,413 B2
(45) Date of Patent: May 21, 2013

(54) CONFIGURING STIMULATION THERAPY USING STIMULATION INTENSITY

(75) Inventors: Richard T. Stone, Minneapolis, MN (US); Steven M. Goetz, North Oaks, MN (US); Gregory F. Molnar, Fridley, MN (US); Gabriela C. Miyazawa, Fridley, MN (US); Martin T. Gerber, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 1211 days.

(21) Appl. No.: 12/111,822

(22) Filed: Apr. 29, 2008

(65) Prior Publication Data
US 2009/0270947 A1    Oct. 29, 2009

(51) Int. Cl.
*A61N 1/00* (2006.01)
(52) U.S. Cl.
USPC .......................................................... 607/62
(58) Field of Classification Search
USPC .................................... 607/28, 46–48, 63, 59
See application file for complete search history.

(56) References Cited

U.S. PATENT DOCUMENTS

| | | | |
|---|---|---|---|
| 4,431,002 A | 2/1984 | Maurer et al. | |
| 5,447,525 A | 9/1995 | Powell et al. | |
| 5,645,573 A | 7/1997 | Kroll et al. | |
| 5,697,956 A * | 12/1997 | Bornzin | 607/28 |
| 6,393,325 B1 | 5/2002 | Mann et al. | |
| 6,516,227 B1 | 2/2003 | Meadows et al. | |
| 6,587,724 B2 | 7/2003 | Mann | |
| 6,609,032 B1 | 8/2003 | Woods et al. | |
| 6,622,048 B1 | 9/2003 | Mann et al. | |
| 6,738,668 B1 | 5/2004 | Mouchawar et al. | |
| 7,050,856 B2 | 5/2006 | Stypulkowski | |
| 7,082,333 B1 | 7/2006 | Bauhahn et al. | |
| 7,127,296 B2 | 10/2006 | Bradley | |
| 7,174,215 B2 * | 2/2007 | Bradley | 607/59 |
| 7,254,444 B2 | 8/2007 | Moore et al. | |
| 2003/0074025 A1 | 4/2003 | Wuthrich | |
| 2004/0143303 A1 * | 7/2004 | Sieracki et al. | 607/48 |
| 2006/0229687 A1 * | 10/2006 | Goetz et al. | 607/46 |
| 2007/0055322 A1 | 3/2007 | Forsberg et al. | |

(Continued)

FOREIGN PATENT DOCUMENTS

| | | |
|---|---|---|
| EP | 0 054 321 | 6/1982 |
| WO | WO 2004/052451 A1 | 6/2004 |
| WO | WO 2008/121891 A1 | 10/2008 |

OTHER PUBLICATIONS

European Search Report dated Mar. 5, 2010 for corresponding European Application No. 09012282.1-2305 (8 pgs.).

(Continued)

*Primary Examiner* — Eric D. Bertram
*Assistant Examiner* — Roland Dinga
(74) *Attorney, Agent, or Firm* — Shumaker & Sieffert, P.A.

(57) ABSTRACT

Techniques for configuring electrical stimulation therapy utilizing one or more stimulation intensity values are described. In one example, a method includes receiving a stimulation intensity value that corresponds to an equal intensity function; determining a pulse width value and a pulse amplitude value based on the equal intensity function; and controlling delivery of electrical stimulation pulses with the determined pulse width value and amplitude value to a patient. A stimulation intensity value may correspond to a plurality of paired pulse width and amplitude values having substantially the same intensity. For example, the plurality of paired pulse width and amplitude values may activate a substantially equal volume of tissue when a stimulation pulse with the paired values is delivered.

28 Claims, 12 Drawing Sheets

U.S. PATENT DOCUMENTS

2007/0083104 A1* 4/2007 Butson et al. .................. 600/407
2007/0288064 A1 12/2007 Butson et al.
2008/0103559 A1* 5/2008 Thacker et al. .................. 607/62

OTHER PUBLICATIONS

Volkmann et al., "Introduction to the Programming of Deep Brain Stimulators," Movement Disorders, vol. 17, No. 3, pp. S181-S187 (2002).

European Examination Report dated Jul. 27, 2011 for Application No. 09012282.1-2305 (5 pgs.).

Office Action dated Nov. 10, 2011 for U.S. Appl. No. 12/429,931, (8 pgs.).

Responsive Amendment dated Feb. 8, 2012 for U.S. Appl. No. 12/429,931, (11 pgs.).

Office Action dated Jul. 31, 2012 for U.S. Appl. No. 12/429,931, (8 pgs.).

Office Action from U.S. Appl. No. 12/429,931, dated Nov. 15, 2012, 8 pp.

Response to Final Office Action dated Jul. 31, 2012, from U.S. Appl. No. 12/429,931, filed Oct. 31, 2012, 13 pp.

Response to Office Action dated Nov. 15, 2012, from U.S. Appl. No. 12/429,931, filed Feb. 15, 2013, 14 pp.

* cited by examiner

CONFIGURING STIMULATION THERAPY USING STIMULATION INTENSITY

TECHNICAL FIELD

The invention relates to medical devices and, more particularly, to configuration of electrical stimulation therapy parameters.

BACKGROUND

Medical devices, such as implantable electrical stimulators, may be used to deliver electrical stimulation therapy to patients to treat a variety of symptoms or conditions such as chronic pain, tremor, Parkinson's disease, epilepsy, urinary or fecal incontinence, sexual dysfunction, obesity, or gastroparesis. In general, such medical devices deliver electrical stimulation therapy in the form of electrical pulses to selected target locations in a patient's body. For example, an implantable electrical stimulator may deliver electrical stimulation via one or more leads that include electrodes located proximate to target tissues of the brain, the spinal cord, pelvic nerves, peripheral nerves, or the stomach of a patient. Hence, stimulation may be used in different therapeutic applications, such as deep brain stimulation (DBS), spinal cord stimulation (SCS), pelvic stimulation, gastric stimulation, or peripheral nerve stimulation. Stimulation also may be used for muscle stimulation, e.g., functional electrical stimulation (FES) to promote muscle movement or prevent atrophy.

In most cases, a clinician selects values for a number of programmable parameters in order to define the electrical stimulation therapy to be delivered by the implantable stimulator to a patient. For example, a clinician may select an amplitude value, which may be a current or voltage amplitude, and a pulse width value for a stimulation waveform of the electrical stimulation therapy to be delivered to the patient. In addition, the clinician may also select a pulse rate or frequency for stimulation pulses to be delivered to the patient, a combination of electrodes carried by one or more implantable leads, and assigns polarities to the selected electrodes. A group of parameters, which can include amplitude, pulse width, pulse frequency, electrode combination and electrode polarity may be referred to as a program in the sense that they drive the electrical stimulation therapy to be delivered to the patient.

In most cases, a clinician creates the one or more programs that a medical device will use to deliver therapy to a patient during an initial programming session. In the case of implantable medical devices, the initial programming session typically occurs shortly after the device is implanted in the patient. The values for each of the parameters of a program may have a significant impact on the efficacy and side effects of the delivery of therapy according to that program. The process of selecting values for the parameters that provide adequate results can be time consuming. In particular, the process may require a great deal of trial-and-error testing of numerous potential combinations of parameter values before a "best" program is discovered. For example, a "best" program may be a program that is better in terms of clinic efficacy versus side effects experienced than other programs tested. As another example, a best program may also be a program that requires relatively less energy than other programs, such that energy consumed by the electrical stimulation is minimized and power source longevity of the medical device is maximized.

In some cases, the clinician may need to test a large number of possible parameter combinations in order to identify a desirable combination of pulse width and amplitude values. For example, the clinician may test pulse width and amplitude combinations by manually specifying a single pulse width value and a single amplitude value for each combination based on intuition or some idiosyncratic methodology. The clinician may then record notes on the efficacy and side effects of each combination after delivery of stimulation via that combination. In some cases, efficacy can be observed immediately within the clinic. For example, spinal cord stimulation may produce paresthesia and side effects that can be observed by the clinician based on patient feedback. In other cases, side effects and efficacy may not be apparent until a program has been applied for an extended period of time, as is sometimes the case in deep brain stimulation. Upon receipt of patient feedback and/or observation of symptoms by the clinician, the clinician is able to compare and select one or more "best" programs from the group of tested programs.

Even after this often-lengthy process, the programs selected during an initial programming session may ultimately prove to be inadequate. The eventual inadequacy of the initial programming may be due to a variety of problems, including progression of symptoms and/or an underlying ailment, increased or changed symptoms or side effects during activities and/or postures that were not replicated in the clinic during the initial programming session, slow onset of side effects and, in the case of delivery of stimulation via electrodes located on implantable leads, lead migration. If the programs selected during an initial programming session prove to be inadequate, the patient must return to the clinic for a follow-up programming session. Multiple follow-up programming sessions may be required over the period of time that the medical device is used to deliver therapy to the patient.

SUMMARY

In general, techniques for configuring electrical stimulation therapy by utilizing one or more stimulation intensity values are described. A single stimulation intensity value may correspond to a plurality of paired pulse width and amplitude values, each pulse width/amplitude pair having a single pulse width value and a single pulse amplitude value. The plurality of pulse width/amplitude value pairs corresponding to one intensity value are different combinations of possible pulse width values with possible amplitude values. All of the pulse width/amplitude pairs corresponding to one intensity value have substantially the same intensity, e.g., delivery of different stimulation pulses with different ones of the paired values would activate a substantially equal volume of tissue.

A pulse width versus amplitude plot of the plurality of paired pulse width and amplitude values that activate a substantially equal volume of tissue may define a curve. For the purposes of this application, a curve defined by a pulse width versus amplitude plot of the plurality of paired pulse width and amplitude values that activate a substantially equal volume of tissue may be referred to as an "equal intensity curve". Further, an "equal intensity function" is a function that defines all points along an equal intensity curve, such that the equal intensity function defines paired pulse width and amplitude values that activate a substantially equal volume of tissue when a stimulation pulse with the paired values is delivered to the tissue. For example, in some embodiments, a stimulation intensity value may correspond to equal intensity function that defines a strength-duration curve in which all points along the strength-duration curve represent paired pulse width and amplitude values that activate a substantially equal volume of tissue when a stimulation pulse with the paired values is delivered to the tissue.

In some examples, an external electrical stimulation programmer may receive a stimulation intensity value for a stimulation pulse, e.g., selected by a user, such as a clinician programming electrical stimulation therapy. Based on the received stimulation intensity value, electrical stimulation parameters may be generated having a pulse width value and amplitude value that is defined by the equal intensity function corresponding to the received stimulation intensity value. The exact pulse width and amplitude values selected from the respective equal intensity values may be based on one or more variables. For example, the one or more variables can be both general and patient specific, and may include, but are not limited to, stimulation efficiency of the electrical stimulation. Further, multiple stimulation intensity values may be provided, with each of the stimulation intensity values corresponding to a different equal intensity function.

In one example, the disclosure provides a method comprising receiving a stimulation intensity value that corresponds to an equal intensity function; determining a pulse width value and a pulse amplitude value based on the equal intensity function; and controlling delivery of electrical stimulation pulses with the determined pulse width value and amplitude value to a patient.

In another example, the disclosure provides a system comprising a medical device that delivers electrical stimulation pulses to a patient; and a processor that receives a stimulation intensity value that corresponds to an equal intensity function, determines a pulse width value and a pulse amplitude value based on the equal intensity function, and controls delivery of electrical stimulation pulses with the determined pulse width value and amplitude value to a patient by the medical device.

In another example, the disclosure provides a system comprising means for receiving a stimulation intensity value that corresponds to an equal intensity function; means for determining a pulse width value and a pulse amplitude value based on the equal intensity function; and means for controlling delivery of electrical stimulation pulses with the determined pulse width value and amplitude value to a patient.

In another example, the disclosure provides a computer-readable storage medium comprising instructions to cause a programmable processor to receive a stimulation intensity value that corresponds to an equal intensity function; determine a pulse width value and a pulse amplitude value based on the equal intensity function; and control delivery of electrical stimulation pulses with the determined pulse width value and amplitude value to a patient.

Examples according to this disclosure may provide for one or more advantages. For example, by providing a stimulation intensity value, a single value may be specified, e.g., by a user programming the stimulation, for a stimulation pulse instead of both a single pulse width value and a single amplitude value for the stimulation pulse. Based on the specified stimulation intensity value, electrical stimulation parameters may be generated having a pulse width and amplitude value that is selected from the plurality of paired pulse width and amplitude values corresponding to the equal intensity function associated with the specified stimulation intensity value. The selected pulse width and amplitude pair may be selected from a plurality of pairs defined by the equal intensity function based on one or more factors as described above. In this manner, the pulse width and amplitude value of a stimulation pulse for electrical stimulation therapy may be programmed by selecting a single intensity value, in addition to taking into account the one or more factors used to select the specific pulse width and amplitude from the equal intensity function associated with the selected intensity value.

As another example, multiple stimulation intensity values may be provided in which each stimulation intensity value corresponds to different equal intensity functions as described above. In this manner, electrical stimulation may be programmed based on monotonically increasing stimulation with respect to stimulation parameters during a programming session, while also taking into account the one or more factors used to select the specific pulse width and amplitude from among the plurality of pairs defined by each of the respective equal intensity functions. Accordingly, in some examples, a user may program stimulation therapy based on intensity, which reflects the relative volume of tissue activated with stimulation, rather than requiring a user to have knowledge of the stimulation intensity resulting from each combination of pulse width and amplitude value that may be input as electrical stimulation parameters for stimulation therapy.

DETAILED DESCRIPTION

Electrical stimulation therapy may provide relief to a patient from many conditions. However, the stimulation therapy efficacy is contingent on a clinician or other user correctly configuring, or programming, the stimulation parameters in a manner that provides appropriate therapy to the patient while minimizing side-effects produced from the stimulation. Due to a number of factors, including physiological diversity, condition differences, and inaccuracies in stimulation lead placement, the parameters may vary greatly between patients. Therefore, typically a clinician must individually program stimulation parameters for each patient. This programming process may continue throughout the therapy as patient needs change.

Figure 1:
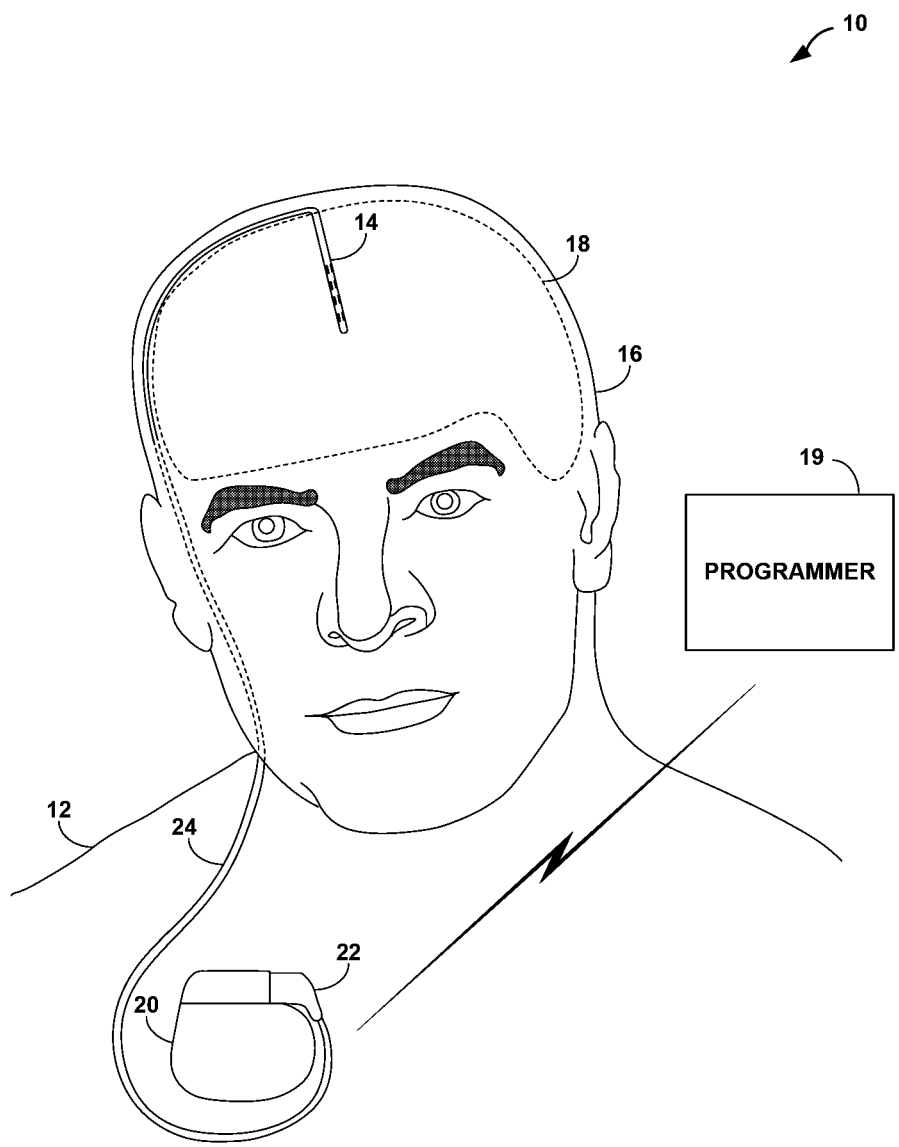
FIG. 1 is a conceptual diagram illustrating an example stimulation system with a stimulation lead implanted in the brain of a patient.

FIG. 1 is a conceptual diagram illustrating an example stimulation system with a stimulation lead implanted in the brain of a patient. As shown in FIG. 1, stimulation system 10 includes implantable medical device (IMD) 20, lead connector 22, lead wire 24 and lead 14 implanted within patient 12. In the illustrated example, lead 14 enters through cranium 16 and is implanted within brain 18 to deliver deep brain stimulation (DBS). One or more electrodes of lead 14 provides electrical pulses to surrounding anatomical regions of brain 18 in a therapy that may alleviate a condition of patient 12. In some examples, an electrode or conductive surface of the housing of IMD 20 may be used with one or more electrodes on lead 14 for delivery of stimulation. In some embodiments, more than one lead 14 may be implanted within brain 18 of patient 12 to stimulate multiple anatomical regions of the brain. As shown in FIG. 1, system 10 may also include a programmer 19, which may be a handheld device, portable computer, or workstation that provides a user interface to a clinician. The clinician interacts with the user interface to program stimulation parameters.

DBS may be used to treat dysfunctional neuronal activity in the brain which manifests as diseases or disorders such as Huntington's Disease, Parkinson's Disease, epilepsy, psychiatric disorders, or movement disorders. Certain anatomical regions of brain 18 are responsible for producing the symptoms of such brain disorders. For example, stimulating an anatomical region, such as the Subthalamic Nucleus, in brain 18 may reduce the number and magnitude of tremors experienced by patient 12. Other anatomical regions may include the globus pallidus interna, globus pallidus externa, ventral intermediate nucleus in thalamus, internal capsule and zona incerta. Anatomical regions such as these are targeted by the clinician during lead 14 implantation. In other words, the clinician attempts to position the lead within or as close to these regions as possible.

While DBS may successfully reduce symptoms of some neurological diseases, the stimulation may cause unwanted side effects as well. Side effects may include incontinence, tingling, loss of balance, paralysis, slurred speech, loss of memory, and many other neurological problems. Side effects may be mild to severe; however, most side effects are reversible when stimulation is stopped. DBS may cause one or more side effects by inadvertently providing electrical stimulation pulses to other anatomical regions or structures near the targeted anatomical region or structure. For this reason, the clinician typically programs the stimulation parameters in order to balance effective therapy and minimal side effects.

Generally, a clinician's primary concern when programming stimulation parameters is the result of the stimulation therapy on the patient rather than the exact parameter values delivered by the simulation therapy that are used to achieve the desired result. Further, the clinician may not be familiar with efficiencies of a specific stimulation therapy system. For example, the efficiency of system 10 may depend at least in part on the specific type of IMD 20 used. An IMD may be more efficient within a certain range or ranges of stimulation parameters values than others, and such ranges may vary as between different IMDs. Additionally, a clinician may not be familiar with the influence that certain stimulation parameters may have on the efficiency of the stimulation therapy. For example, efficiency of the stimulation therapy may vary depending on the pulse width value and amplitude value that the stimulation therapy is delivered. Furthermore, an IMD may have interlocks or limitations on settings that a user may not be familiar with. For example, at a given pulse frequency, electrode combination and impedance, it may be possible to increase one but not both of the pulse width and amplitude due to the interlocks or limitations of a particular IMD. Similarly, although not necessarily known by a user, certain stimulation parameter settings may exceed physiological or tissue safety limits, e.g., relating to charge density.

In accordance with this disclosure, system 10 may utilize one or more stimulation intensity values to configure electrical stimulation therapy delivered to patient 12. In general, a single stimulation intensity value may be selected, e.g., by a clinician, for stimulation therapy rather than a pulse width value and an amplitude value. For example, a clinician may interact with the user interface of programmer 19 to manually input a stimulation intensity value for the electrical stimulation to be delivered via one or more electrodes of lead 14. Programmer 19 receives the stimulation intensity value selected by the clinician and generates stimulation parameters that include a pulse width value and an amplitude value based on the received stimulation intensity value. The stimulation parameters generated by programmer 19 are transmitted to IMD 20, which delivers the electrical stimulation via lead 14.

Figure 2:
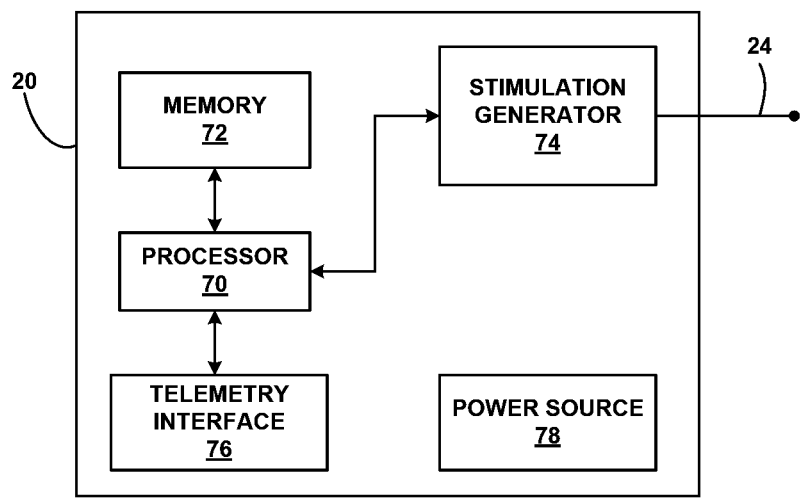
FIG. 2 is a block diagram illustrating an example implantable medical device for delivery of electrical stimulation therapy.

FIG. 2 is a functional block diagram of an example implantable medical device that generates electrical stimulation signals. FIG. 2 illustrates components of IMD 20, which can be utilized by IMD embodiments described herein. In the example of FIG. 2, IMD 20 includes a processor 70, memory 72, stimulation generator 74, telemetry interface 76, and power source 78. As shown in FIG. 2, stimulation generator 74 is coupled to lead wire 24 (and thereby to lead 14). Alternatively, stimulation generator 74 may be coupled to a different number of leads as needed to provide stimulation therapy to patient 12.

Processor 70 controls stimulation generator 74 to deliver electrical stimulation therapy according to programs stored in memory 72 and/or received from programmer 19 via telemetry interface 76. In some cases, a program received from programmer 19 may in fact be a modification of one or more stimulation parameters of an existing program in memory 72. As an example, a program received from programmer 19 may modify the pulse width and amplitude of stimulation in accordance with stimulation intensity value received by programmer 19. Processor 70 may control stimulation generator 74 to modify the pulse width and amplitude of stimulation. Processor 70 may also store these values in memory 72 to continue providing stimulation with the new pulse width and amplitude. Processor 70 may stop the previous program before starting the new stimulation program as received from programmer 19. In some examples, the amplitude of the stimulation signal may be ramped down or ramped up as a program is being turned off or turned on. In this manner, no abrupt stimulation changes may be perceived by patient 12. A ramp up of the new program may provide patient 12 time to stop stimulation if the new program is uncomfortable or even painful.

Processor 70 may comprise any one or more of a microprocessor, digital signal processor (DSP), application specific integrated circuit (ASIC), field-programmable gate array (FPGA), or other digital logic circuitry. Memory 72 stores instructions for execution by processor 70, e.g., instructions that when executed by processor 70 cause the processor and IMD 20 to provide the functionality ascribed to them herein, as well as stimulation programs. Memory 72 may include any one or more of a random access memory (RAM), read-only memory (ROM), electronically-erasable programmable ROM (EEPROM), flash memory, or the like.

Stimulation generator 74 may provide stimulation in the form of pulses to patient 12. Alternatively, stimulation generator 74 may provide therapy in the form of some continuous signal such as a sine wave or other non-pulse therapy. Stimulation parameters for each stimulation program may include electrode configuration, current or voltage amplitude, pulse width, pulse frequency, and/or duty cycle. Other parameters may be used depending on the therapy to be provided to patient 12. Stimulation generator 74 may independently utilize any combination of electrodes on any number of leads 14. In this manner, stimulation generator 74 may be utilized to deliver stimulation via numerous different electrode configurations to provide therapy for a wide variety of patient conditions. In addition, stimulation generator 74 may test the functionality of electrodes on lead 14. Based upon the impedance testing, specific electrodes may be removed from possible use in therapy when the test indicates that the impedance is above or below normal operating limits.

Telemetry interface 76 may include circuitry known in the art for facilitating wireless telemetry, e.g., via radio frequency (RF) communication or proximal inductive interaction with similar circuitry within external programmer 19. Power source 78 delivers operating power to the components of IMD 20. Power source 78 may include a battery and a power generation circuit to produce the operating power. In some embodiments, the battery may be rechargeable to allow extended operation. Recharging may be accomplished through proximal inductive interaction between an external charger and an inductive charging coil within IMD 20. In other embodiments, non-rechargeable batteries may be used. As a further alternative, an external power supply could transcutaneously power IMD 20 whenever stimulation is needed or desired.

Figure 3:
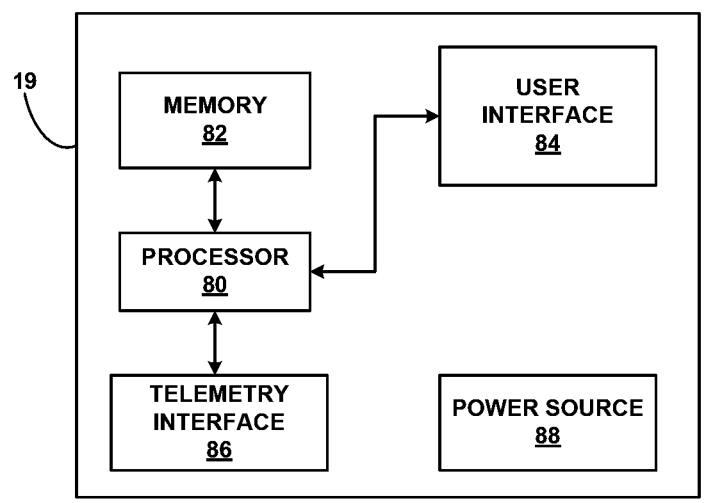
FIG. 3 is a block diagram illustrating an example programmer for programming and controlling the implantable medical device of FIG. 2.

FIG. 3 is a functional block diagram of an example programmer. As shown in FIG. 3, external programmer 19 includes processor 80, memory 82, user interface 84, telemetry interface 86, and power source 88. Programmer 19 may be used to present one or more stimulation intensity values to the user via user interface 84, or otherwise provide media for selection stimulation intensity values via user interface 84. Programmer 19 may also determine stimulation parameter values in accordance with a received stimulation intensity value, and transmit the stimulation parameter values, e.g., as one or more programs, to IMD 20. As described herein, programmer 19 may allow a clinician to select a stimulation intensity value, and generate stimulation parameters based on the received stimulation intensity value. For example, as described herein processor 80 may store stimulation parameters as one or more programs in memory 82. Processor 80 may send programs or parameter values to IMD 20 via telemetry interface 86 to control stimulation automatically and/or as directed by the user.

Programmer 19 may be one or both of a clinician programmer or a patient programmer, i.e., the programmer may be configured for use depending on the intended user. A clinician programmer may include more functionality than the patient programmer. For example, a clinician programmer may include a more featured user interface, allow a clinician to download usage and status information from IMD 20, and allow a clinician to control aspects of the IMD not accessible by a patient programmer embodiment of programmer 19.

A user, either a clinician or patient 12, may interact with processor 80 through user interface 84. Any of the user interface embodiments described herein may be embodiments of user interface 84, such as user interface 1100 of FIG. 11. User interface 84 may include a display, such as a liquid crystal display (LCD), light-emitting diode (LED) display, or other screen, to show information related to stimulation therapy, and buttons or a pad to provide input to programmer 19. In embodiments where user interface 84 requires a 3D environment, the user interface may support 3D environments such as a holographic display, a stereoscopic display, an autostereoscopic display, a head-mounted 3D display, or any other display that is capable of presenting a 3D image to the user. Buttons may include an on/off switch, plus and minus buttons to zoom in or out or navigate through options, a select button to pick or store an input, and pointing device, i.e. a mouse, trackball, pointstick or stylus. Other input devices may be a wheel to scroll through options or a touch pad to move a pointing device on the display. In some embodiments, the display may be a touch screen that enables the user to select options directly from the display screen.

Processor 80 processes instructions from memory 82 and may store user input received through user interface 84 into the memory when appropriate for the current therapy. In addition, processor 80 provides and supports any of the functionality described herein with respect to each embodiment of user interface 84. Processor 80 may comprise any one or more of a microprocessor, digital signal processor (DSP), application specific integrated circuit (ASIC), field-programmable gate array (FPGA), or other digital logic circuitry.

Memory 82 may include instructions for operating user interface 84, telemetry interface 86 and managing power source 88. The instructions may include a set of equations needed to characterize brain tissue and interpret stimulation field dimensions. Memory 82 may include any one or more of a random access memory (RAM), read-only memory (ROM), electronically-erasable programmable ROM (EEPROM), flash memory, or the like. Processor 80 may comprise any one or more of a microprocessor, digital signal processor (DSP), application specific integrated circuit (ASIC), field-programmable gate array (FPGA), or other digital logic circuitry.

Memory 82 may store program instructions that, when executed by processor 80, cause the processor and programmer 19 to provide the functionality ascribed to them herein. For example, memory 82 may also include instructions for generating stimulation parameters based on a received stimulation intensity value. These instructions may include one or more equations that determine and define a plurality of paired pulse width and amplitude values that correspond to respective stimulation intensity values. For example, memory may include one or more equal stimulation intensity functions that define a plurality of paired pulse width and amplitude values that correspond to respective stimulation intensity values.

In some embodiments, memory may include experimentally determined data sets that include a plurality of paired pulse widths and amplitude values that correspond to respective stimulation intensity values. Further, the memory may include one or more instructions used to generate a stimulation parameter from a received stimulation intensity value. For example, memory may include instruction for determining which plurality of paired pulse width and amplitude values, e.g., as defined by a respective equal stimulation function, corresponds to the received stimulation intensity value. An equal stimulation intensity function corresponding to a stimulation intensity value is not limited to an equation, and may include a data set comprising a plurality of paired pulse width and amplitude values, such as a look-up table, stored in memory 82. In other words, the term "function" as used herein is not limited to equations, but may include such data sets.

In addition, the memory may contain instructions for determining which individual pulse width and amplitude value pair is selected from the plurality of paired pulse widths and amplitude values corresponding to the received stimulation intensity value. For example, these instructions may allow for a determination to be made according to one or more variables, e.g., stimulation efficiency. In some embodiments, memory 82 does not contain instructions for all functionality for the user interfaces and programming of stimulation parameters as described herein. In this case, memory 82 may only hold the necessary instructions for the specific embodiment that the user desires. Memory 82 may be reformatted with different sets of instructions when needed.

Wireless telemetry in programmer 19 may be accomplished by radio frequency (RF) communication or proximal inductive interaction of programmer 19 with IMD 20. This wireless communication is possible through the use of telemetry interface 86. Accordingly, telemetry interface 86 may include circuitry known in the art for such communication.

Power source 88 delivers operating power to the components of programmer 19. Power source 88 may include a battery and a power generation circuit to produce the operating power. In some embodiments, the battery may be rechargeable to allow extended operation. Recharging may be accomplished through proximal inductive interaction, or electrical contact with circuitry of a base or recharging station. In other embodiments, primary batteries may be used. In addition, programmer 19 may be directly coupled to an alternating current source, such would be the case with a stationary workstation for 3D visualization environments.

In some embodiments, the user interface may be used to, but is not necessarily used to, provide real-time programming of IMD 20. For example, the clinician may use the user interface to select a stimulation intensity value, and programmer 19 automatically or semi-automatically generates stimulation parameters having a pulse width and amplitude value associated with received stimulation intensity value. However, in some examples, stimulation therapy with the generated parameters may not be delivered at the same time. Instead, the stimulation therapy may be delivered after the clinician has determined the stimulation therapy should be delivered to the patient. In this manner, stimulation therapy perceived by patient 12 does not change at the same time the clinician changes the stimulation intensity value.

In other examples, the user interface may be used as such in a real-time programming environment to provide immediate feedback to the clinician or patient. For example, a programmer may generate stimulation parameters consistent with a received stimulation intensity value and stimulation therapy having those parameters may be delivered at the approximately the same time a clinician or patient selects the stimulation intensity value. In this manner, stimulation therapy perceived by patient 12 may change at approximately the same time the user changes the stimulation intensity value.

System 10 (FIG. 1) may also include multiple leads 14 or electrodes on leads of other shapes and sizes. The user interface may allow the clinician to program each lead simultaneously or require the clinician to program each lead separately. In some DBS patients, two leads 14 are implanted at symmetrical locations within brain 18 for bilateral stimulation. In particular, a first lead may be placed in the right hemisphere of brain 18 and a second lead may be placed at the same location within the left hemisphere of the brain. In some embodiments, a clinician may be able to select a single stimulation value that the programmer generates stimulation parameters based on for all leads in system 10. In other embodiments, a clinician may be able to select a separate stimulation intensity value that the programmer generates stimulation parameters for each lead or combination of leads in system 10.

While lead 14 is described for use in DBS applications throughout this disclosure as an example, lead 14, or other leads, may be implanted at any other location within patient 12. For example, lead 14 may be implanted near the spinal cord, pudendal nerve, sacral nerve, or any other nervous or muscle tissue that may be stimulated. For example, such tissues may include those tissues associated with a patient's central nervous system or peripheral nervous system, including peripheral nerves and peripheral nerve fields.

System 10 may allow pulse width and amplitude values of stimulation pulses to be programmed using one or more stimulation intensity values. In some examples, a clinician may select a stimulation intensity value from a plurality of possible stimulation intensity values via user interface 84 of programmer 19, which generates stimulation parameters values for pulse width and amplitude based on the received stimulation intensity value. Each stimulation intensity value may correspond to a different plurality of paired pulse width and amplitude values for an electrical stimulation pulse. Further, each individual pulse width and amplitude value pair in a respective plurality of paired pulse width and amplitude values all may activate a substantially equal volume of tissue with the stimulation pulse. Consequently, each stimulation intensity value may be representative of the relative volume of tissue activated with electrical stimulation in accordance with the stimulation intensity value.

In some embodiments, memory 82 stores data defined by one or more equal intensity functions that corresponds to respective stimulation intensity values. As described herein, an equal intensity function may define the plurality of paired pulse width and amplitude values that correspond to a stimulation intensity value. In this manner, a pulse width versus amplitude plot of the equal intensity function can define an equal intensity curve that includes the plurality of coupled pulse width and amplitude values that correspond to the respective stimulation intensity value.

Figure 4:
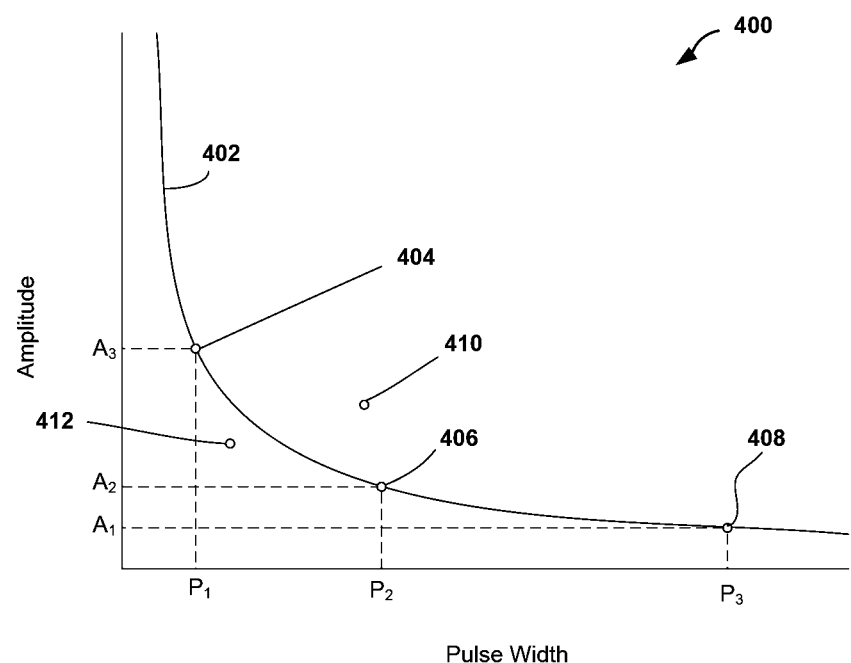
FIG. 4 is diagram illustrating an example equal intensity function which may correspond to a specific stimulation intensity value.

FIG. 4 is a diagram illustrating an example equal intensity function which may correspond to a specific stimulation intensity value. In general, diagram 400 includes a pulse width versus amplitude plot of the example equal intensity function that results in equal intensity curve 402. Subject to one or more limitations that will be described below, all points along curve 402 define paired pulse width and amplitude values that activate a substantially equal volume of tissue with a stimulation pulse. For example, a stimulation pulse having a pulse width of $P_1$ and an amplitude of $A_3$, i.e., point 404, and a stimulation pulse having a pulse width of $P_2$ and an amplitude of $A_2$, i.e., point 406, activate a substantially equal volume of tissue when delivered as electrical stimulation. As another example, a stimulation pulse having a pulse width of $P_1$ and an amplitude of $A_3$, i.e., point 404, and a stimulation pulse having a pulse width of $P_3$ and an amplitude of $A_1$, i.e., point 408, activate a substantially equal volume of tissue when delivered as electrical stimulation. In this manner, points 404, 406, 408 define three pulse width and amplitude value pairs, i.e., paired pulse width and amplitude values, which may correspond to a single stimulation intensity value.

Furthermore, as indicated by FIG. 4, point 410 and point 412 are not points along curve 402. Accordingly, each of points 410 and 412 define a respective pulse width and amplitude value pair that do not activate a substantially equal volume of tissue when a stimulation pulse is delivered with the paired amplitude and pulse width values, either with each other, or with paired pulse width and amplitude values on curve 402. Instead, in this case, point 412 defines a pulse width and amplitude value pair that may activate a lesser volume of tissue than points on curve 402, and point 410 defines a pulse width and amplitude value pair that may activate a greater volume of tissue with a stimulation pulse than points on curve 402. Accordingly, while points 410 and 412 define paired pulse width and amplitude values that do not correspond to the same stimulation intensity value as points 404, 406, 408, the respective points may define paired values correspond to two different respective stimulation intensity values.

As noted, there may be one or more limitations to the statement that all points along 402 define paired pulse width and amplitude values activate a substantially equal volume of tissue. For example, there may be a minimum pulse width along curve 402 that is required to activate a volume of tissue. In general, if a stimulation pulse has a pulse width that is less than this minimum pulse width, the stimulation pulse will likely by unable to activate the volume of tissue no matter how much the amplitude is increased. Similarly, there may be a minimum amplitude along curve 402 that is required to activate a volume of tissue. In some cases, this minimum amplitude may be known as the rheobase amplitude. Additionally, the pulse width value corresponding to twice the rheobase amplitude may be known as the chronaxie. For the purposes of illustration, if point 408 was determined to define the minimum amplitude required to activate tissue, the rheobase amplitude would be a value of $A_1$ and the chronaxie would be a pulse width of $P_2$, assuming that $A_2$ is twice that of $A_1$.

Although all points on curve 402, including 404, 406, 408, define individual pulse width and amplitude value pairs that activate a substantially equal volume of tissue when electrical stimulation is delivered with those values (subject to at least the minimum amplitude and pulse width limitations described herein), the individual paired pulse width and amplitude values are not necessarily substantially equal in all other aspects. For example, stimulation efficiency can vary depending on the pulse width and amplitude value of the stimulation.

Figure 5:
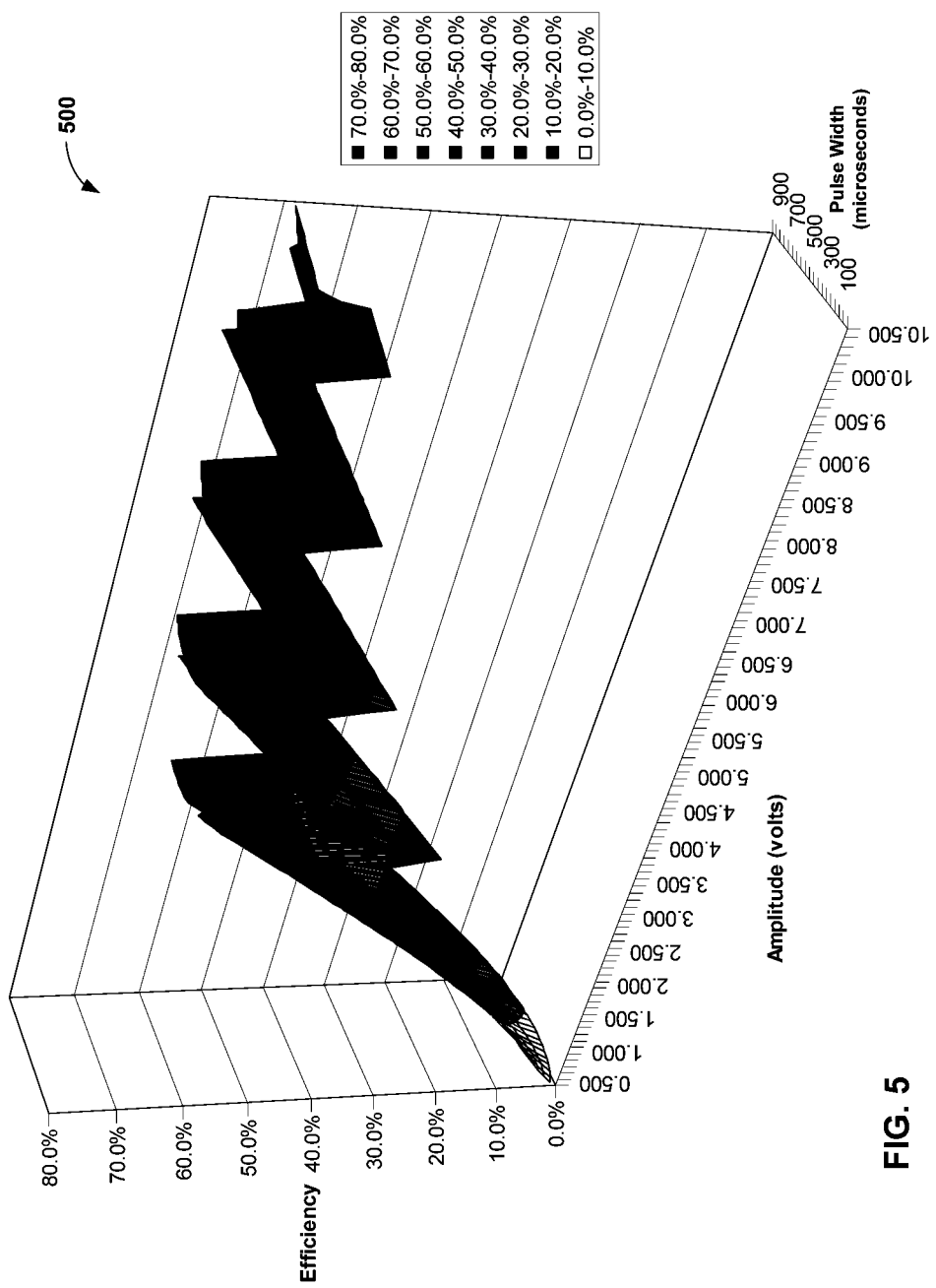
FIG. 5 is a three-dimensional plot illustrating an example relationship between pulse width, amplitude and efficiency of a stimulation pulse.

FIG. 5 is a three-dimensional plot illustrating an example relationship between pulse width, amplitude, and stimulation therapy efficiency. As indicated by FIG. 5, one axis of plot 500 contains a range of pulse width values in microseconds. Another axis of plot 500 contains a range of amplitude values in volts. Another axis of plot 500 contains a range of stimulation efficiency as a percentage of maximum.

In general, plot 500 illustrates that stimulation efficiency may be dependant on both amplitude and pulse width. Notably, plot 500 illustrates that efficiency both increases and decreases over certain amplitude ranges as amplitude is increased from a value of 0.5 volts to 10.5 volts at a constant pulse width. Plot 500 also illustrates that efficiency may both increase and decrease over certain pulse width ranges as pulse width is increased from a value of 100 microseconds to 900 microseconds at a constant amplitude.

In general, stimulation efficiency relates to the amount of energy from power source 78 (FIG. 2) used for delivery of stimulation pulses with the specified pulse amplitude and width. Although various pulse width/amplitude pairs associated with a common stimulation intensity value may activate a substantially equal volume of tissue, delivery of stimulation pulses with the different paired values may consume different amounts of energy from the power source. Thus, one factor that may be used to determine the stimulation efficiency value shown in FIG. 5 is the influence that the stimulation has on the life of a power source of an IMD.

In general, the power source life of an IMD may vary depending on pulse width and amplitude value of stimulation. With respect to curve 402, for example, stimulation according to the paired pulse width and amplitude value defined by point 406 may consume relatively less power than stimulating according to the paired pulse width and amplitude value defined by point 404. Furthermore, stimulation according to the paired pulse width and amplitude value defined by point 406 may consume relatively less power than stimulation according to all other points along curve 402.

The difference in power source consumption between different pulse width and amplitude pairs may be due, at least in part, to the configuration of stimulation generator 74. In particular, stimulation generator 74 may require the same energy from power source 78 in order to produce any amplitude value within a range, and there may be a plurality of such ranges, each range requiring a respective amount of energy from power source 78. These ranges may, for example, correspond to different configurations of a stack of capacitors of stimulation generator 74 used to select the amount of energy drawn from power source 78 for delivery of a stimulation pulse. The possible configurations of the capacitor stack may be more limited then the desired granularity of possible amplitude values output by stimulation generator 78. The lower an amplitude is within a range of amplitude values associated with a particular configuration of the capacitor stack, the less efficient that amplitude value will be with respect to the consumption of energy from power source 78. Such inefficiency associated with the limited configurability of a capacitor stack may be referred to as voltage doubling inefficiency.

As another example, the current voltage level of a power source relative to the voltage necessary to create a stimulation pulse having a certain voltage amplitude may influence stimulation efficiency. For example, in some cases, if the voltage necessary to create a stimulation pulse is greater than the current voltage of a power source, then the voltage level must be multiplied or boosted. In general, the more boost required, the less efficient the respective stimulation. As another example, in some cases, if the voltage necessary to create a stimulation pulse is less than the current voltage of a power source, then "bucking," e.g. drawing a voltage less than that of a power source, may be required. In general, the more bucking required, the less efficient the respective stimulation.

The relative stimulation efficiency of various pulse width and amplitude pairs may be influenced by the current voltage level of a power source, which may change over time. The current voltage level of a power source may influence both stimulation efficiency differences due to a configuration of a stimulation generator, and those due to boosting or bucking. Because the current voltage level of a power source may change over time, e.g., over a relatively long period of time for a primary cell device or a short period of time for a rechargeable device, the relative stimulation efficiency of various pulse width and amplitude pairs may also vary over time.

The internal resistance of a power source may also influence the relative stimulation efficiency of various pulse width/amplitude pairs. Furthermore, as the internal resistance of a power source may increase with age and/or use, the relative stimulation efficiencies may again vary over time. For example, this factor may result in a relative stimulation efficiency increase for amplitude and pulse width pairs having relatively lower amplitudes.

As another example, the time available for an IMD to prepare for a stimulation pulse may influence stimulation efficiency. For example, relatively short amounts of time between pulses, e.g., as a result of relatively long pulse widths or relatively high pulse frequency, may require a relatively high voltage level to get stimulation capacitors to the required stimulation amplitude value in time for pulse to be delivered. In this manner, the stimulation efficiency of a stimulation pulse having a long pulse width may be less efficient compared to a stimulation pulse having a relatively short pulse width delivered at the same pulse frequency.

Figure 6:
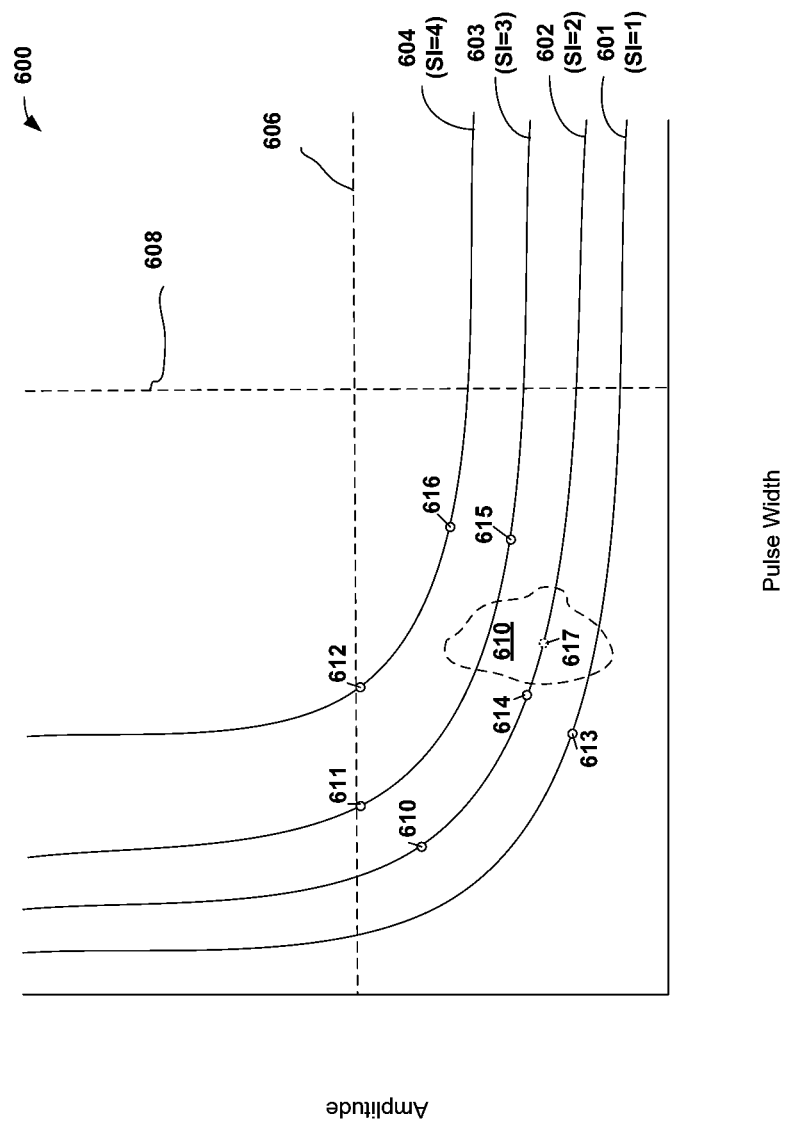
FIG. 6 is a plot of three example strength-duration curves associated with three example stimulation intensity values.

FIG. 6 is a diagram illustrating a plurality of example equal intensity functions corresponding to a plurality of stimulation intensity values. In general, diagram 600 includes pulse width versus amplitude plots of four different equal intensity functions that result in equal intensity curves 601, 602, 603, and 604. As shown, each of the respective curves corresponds to a different stimulation intensity value. In particular, curve 601 corresponds to a stimulation intensity value of 1, curve 602 corresponds to a stimulation intensity value of 2, curve 603 corresponds to a stimulation intensity value of 3, and curve 604 corresponds to a stimulation intensity value of 4.

In general, each of the respective curves defines a plurality of paired pulse width and amplitude values that activate a substantially equal volume of tissue when a stimulation pulse having the values is delivered to the tissue. Further, according to the diagram, the volume of tissue activated with a stimulation pulse according to the respective curves may increase incrementally from curve 601 to curve 602 to curve 603 to curve 604. Consequently, an electrical stimulation pulse having a pulse width and amplitude value that corresponds to a stimulation intensity value of 2 may activate a greater volume of tissue than an electrical stimulation pulse having a pulse width and amplitude that corresponds to a stimulation intensity value of 1; an electrical stimulation pulse having a pulse width and amplitude value that corresponds to a stimulation intensity value of 3 may activate a greater volume of tissue than an electrical stimulation pulse having a pulse width and amplitude that corresponds to a stimulation intensity value of 2; and an electrical stimulation pulse having a pulse width and amplitude value that corresponds to a stimulation intensity value of 4 may activate a greater volume of tissue than an electrical stimulation pulse having a pulse width and amplitude that corresponds to a stimulation intensity value of 3.

In some embodiments, data defined by the example equal intensity functions illustrated by FIG. 6 may be stored in memory 82 of programmer 19. In such cases, programmer 19 may be used to configure electrical stimulation therapy by utilizing the stimulation intensity values that correspond to the data defined by the respective equal intensity function. For example, pulse width and amplitude values for electrical stimulation may be selected by programmer 19 based on a received stimulation intensity value and such data stored in memory 82. Although FIG. 6 illustrates four curves corresponding to four intensity values, other examples may include greater or fewer curves corresponding to greater or fewer possible stimulation intensity values.

Figure 7:
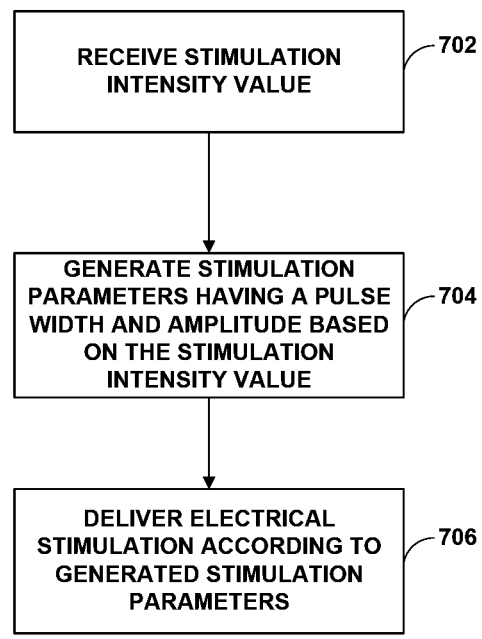
FIG. 7 is a flow diagram illustrating an example technique for controlling delivery of electrical stimulation based on a stimulation intensity value.

FIG. 7 is a flow diagram illustrating an example technique for controlling delivery of electrical stimulation based on stimulation intensity values. In this case, the example technique of FIG. 7 is described with reference to diagram 600 of FIG. 6 that includes curves 601, 602, 603, 604 which are plots of four equal intensity functions corresponding to stimulation intensity values of 1, 2, 3, and 4, respectively. Additionally, the example technique of FIG. 7 is also described with reference to system 10 illustrated in FIGS. 1-3. Notwithstanding, the technique may be applied to a variety of situations, device, and systems, including those described herein. For example, in some embodiments the technique may be applied by processor 70 of IMD 20.

In the example illustrated by FIG. 7, processor 80 of programmer 19 receives a stimulation intensity value (702), e.g., from a user utilizing system 10 to deliver stimulation therapy to patient 12. In some cases, user interface 84 of programmer 19 may graphically present one or all of the stimulation intensity values such that the user may select a stimulation intensity value for the electrical stimulation. The presentation may be in the form of any of a variety media for selection of a stimulation intensity value, such as a drop-down menu, slider bar, up and down arrows, or any other manipulable graphical representation of stimulation intensity. Upon receiving the stimulation intensity value, processor 80 generates stimulation parameters that have a pulse width and amplitude value based on the received stimulation intensity value (704). For example, processor 80 may receive a stimulation value of "2" from a user via user interface 84. As previously described, a stimulation value of "2" corresponds to the equal intensity function illustrated by curve 602 of FIG. 6, which defines a plurality of paired pulse width and amplitude values that activate a substantially equal volume of tissue. Accordingly, processor 80 may generate the stimulation parameters (704) by selecting one of the pulse width and amplitude value pairs of the plurality of paired pulse width and amplitude values represented by curve 602.

Figure 8:
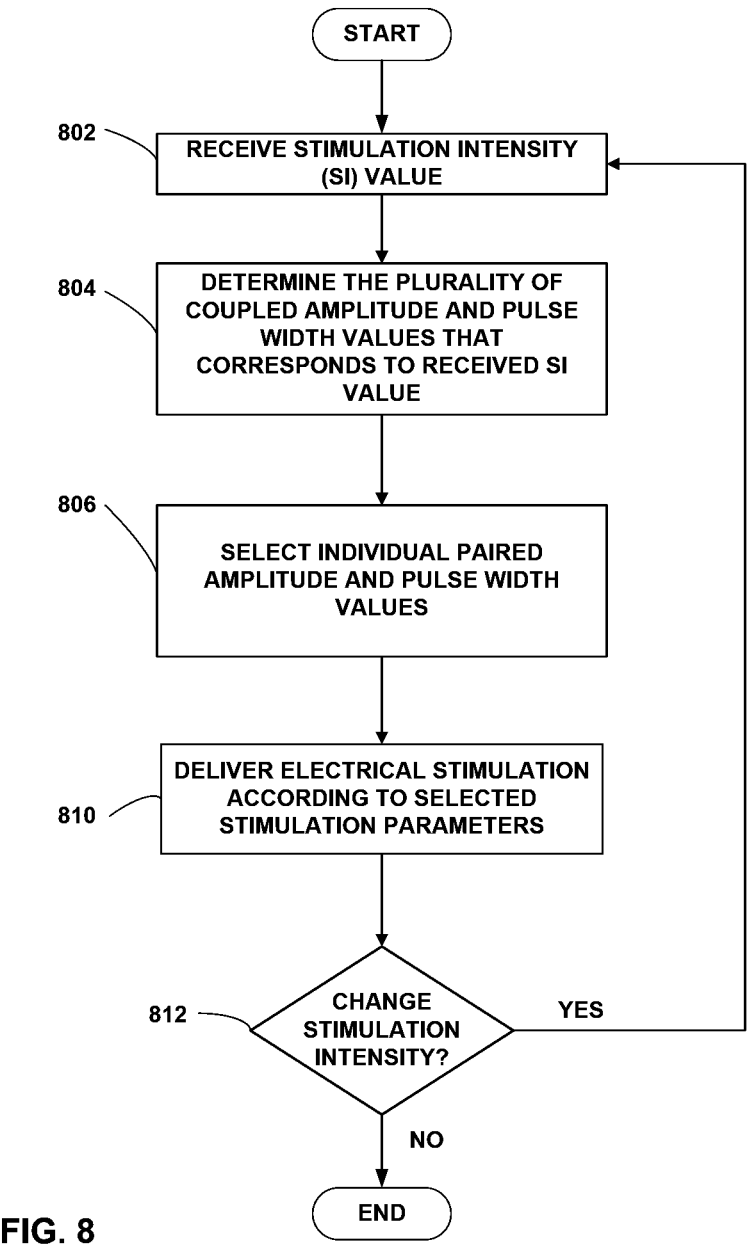
FIG. 8 is a flow diagram illustrating an example technique for controlling delivery of electrical stimulation based on stimulation intensity values.

The determination of which paired pulse width and amplitude value of the plurality of paired pulse width and amplitude values to select can depend on one or more factors, and is discussed in further detail with respect to FIG. 8. Still referring to FIG. 7, in some embodiments, the generated stimulation parameters may be included in a stimulation program. Processor 80 may transmit the stimulation program including the generated stimulation parameters to IMD 20 via telemetry interface 86. Processor 82 may also additionally or alternatively cause the stimulation program including the generated stimulation parameters to be stored in memory 82.

Processor 70 of IMD 20 receives the stimulation program via telemetry interface 76. Subsequently, processor 70 causes stimulation generator 74 to generate and deliver electrical stimulation according to the received stimulation program, which includes the stimulation parameters generated by programmer 19, to patient 12 via lead 14 (706). In this manner, the technique illustrated by FIG. 7 may allow electrical stimulation therapy to be configured by utilizing one or more stimulation intensity values. More specifically, the technique may allow a stimulation parameters having a pulse width and amplitude to be generated based on a single received stimulation intensity value.

FIG. 8 is a flow diagram illustrating an example technique for controlling delivery of electrical stimulation based on stimulation intensity values. In accordance with the example shown in FIG. 8, a technique may involve the selection of more than one stimulation intensity value to program stimulation therapy parameters, e.g., during a stimulation programming session. Similar to the technique illustrated by FIG. 7, the example technique of FIG. 8 is described with reference to diagram 600 of FIG. 6 that includes curves 601, 602, 603, 604, which are plots of four equal intensity functions corresponding to stimulation intensity values of 1, 2, 3, and 4, respectively. Additionally, the example technique of FIG. 8 is also described with reference to system 10 illustrated in FIGS. 1-3. Notwithstanding, the technique may be applied to a variety of situations, device, and systems, including those described herein. For example, in some embodiments the example technique of FIG. 8 may be applied by processor 70 of IMD 20.

As illustrated by FIG. 8, processor 80 of programmer 19 receives a stimulation intensity value (802), e.g., from a user utilizing system 10 to deliver stimulation therapy to patient 12. As previously described, user interface 84 may graphically present one or all of the stimulation intensity values such that the user may select a stimulation intensity value for the electrical stimulation. For example, user interface 84 may graphically present all four stimulation intensity values, i.e., 1, 2, 3, and 4, to a user, who selects a stimulation value desired for the stimulation program.

A user selection may depend on a number of one or more factors. For example, the user may begin by selecting a stimulation intensity value that represents relatively low stimulation intensity. In some cases, the lowest stimulation intensity value may be selected and automatically increase until a specified effect is elicited. As another example, a user may select a stimulation intensity value based on patient specific factors, such as stimulation intensity value that was identified as the minimum value that elicited noticeable results in a patient during a previous calibration session. In some cases, the initial stimulation intensity may correspond to a present or past therapy for the patient. Further, initial stimulation intensity value selection may be determined based on diagnostic indication, disease state or other aspect of patient demographics. As another example, a user may select a stimulation intensity value based on electrode location, and, more generally, stimulation lead 14 location. In some cases, stimulation intensity may be selected based on the known spatial relationship between the active electrode(s) and target tissue. As another example, a stimulation intensity value may be selected based on a previous recorded preference for a specific user, programmer or clinic. As another example, an user may select a stimulation intensity value that based on the stimulation device, e.g., a stimulation intensity that includes stimulation parameters having the maximum, or a relatively high, stimulation efficiency for the device.

After receiving the stimulation intensity value, processor 82 determines the plurality of pulse width and amplitude value pairs that correspond to the received stimulation intensity value (804). In some embodiments, processor 82 may use instructions stored in memory 82 to determine the plurality of corresponding paired pulse width and amplitude values. For example, instructions in memory 82 may specify that the stimulation intensity value of "2" corresponds to a specific equal intensity function, also contained in memory 82, which defines the plurality of paired pulse width and amplitude values. For example, curve 602 may represent the equal intensity function stored in memory 82 that corresponds to a simulation intensity value of "2".

Once processor 80 determines the plurality of pulse width and amplitude value pairs that correspond to the received stimulation intensity value (804), processor 80 selects one of the paired pulse width and amplitude values (806) from the plurality of paired pulse width and amplitude values determined to correspond to the stimulation intensity value (804).

Processor 80 may select one of the pulse width and amplitude value pairs based on instructions stored in memory 82. The instructions may allow the selection to take into account one or more factors. In some embodiments, stimulation efficiency of each pulse width and amplitude value pair may be taken into account. For example, the selected pair may have the highest stimulation efficiency.

In some embodiments, the factors taken into account in selecting one of the plurality of paired pulse width and amplitude values associated with one stimulation intensity value may cause entire ranges of pulse width and amplitude values to be excluded. Line 606 in FIG. 6 represents an example upper limit for the amplitude value such that processor will not select any paired pulse width and amplitude values having an amplitude greater than or equal to the amplitude value of line 606. Similarly, line 608 in FIG. 6 represents an example upper limit for the pulse width value such that processor will not select any paired pulse width and amplitude value having a pulse width greater than or equal to the pulse width value of line 608.

Although lines 606 and 608 represent upper limits, embodiments of the present invention may also include lower limits for the respective values. As another example, area 610 in FIG. 6 represents a range of pulse width and amplitude values that are excluded. In some embodiments, area 610 may represent a certain range of pulse width and amplitude values that are known to cause one or more side-effects or other negative result. Such an area may be patient specific, therapy or disease state specific, or electrode location specific.

Furthermore, selection of the particular pulse width/amplitude pair from an equal intensity function may be based on other factors instead of or in addition to stimulation efficiency and side effects. Examples include physiological guidelines, device capabilities, interlocks, or the like, as described above. As another example, in some embodiments, certain pairs may be preferred based on the type of tissue which is intended to be activated with the stimulation. For example, the pulse width of stimulation may affect the ability of the stimulation to capture neural tissue with certain fiber diameter widths. For this reason, pairs with higher or lower pulse widths may be preferred based on the fiber diameter of neural tissue that is intended to be activated with stimulation.

Additionally, the equal intensity functions may themselves be different depending on the tissue to which stimulation is delivered. For example, different effects of particular values or ranges of pulse width and amplitude on different type(s) of tissues may affect the volume of tissue activated, depending on to what type(s) of tissue the stimulation is delivered. Thus, for example, equal intensity functions may vary depending on the fiber diameters, or predominant fiber diameter, for neural tissue to which the stimulation is delivered.

Processor 80 may then transmit stimulation parameters including the selected pulse width and amplitude pair to IMD 20 via telemetry interface 86. IMD 20 may then deliver electrical stimulation according to the stimulation parameters (810) to patient 12 via lead 14.

In some examples, the stimulation intensity value may be changed one or more times. For example, as indicated by FIG. 8, a user may decide to change the stimulation intensity value (812) after electrical stimulation has been delivered for some time at a current stimulation intensity value. A user may select a new stimulation intensity value, e.g., to increase or decrease the stimulation intensity, using programmer 20.

In such cases, processor 80 may receive the stimulation intensity value (802); determine the plurality of coupled pulse width and amplitude values that correspond to the received value (804); select the paired pulse width and amplitude values from the plurality of paired pulse width and amplitude values that correspond to the stimulation intensity value (806); and deliver electrical stimulation with the selected pulse width and amplitude values (810), all substantially as described herein.

Using such a technique, electrical stimulation therapy may be configured by utilizing one or more stimulation intensity values. More specifically, the technique may allow a stimulation parameters having a pulse width and amplitude to be generated based on a single received stimulation intensity value which may be changed, e.g., to help determine the desirable intensity level for stimulation.

Referring to FIG. 6, diagram 600 may be used to illustrate example scenarios in which stimulation therapy parameters are configured using stimulation intensity values. As previously explained, curves 601, 602, 603, and 604 may correspond to stimulation intensity values of 1, 2, 3, and 4, respectively. Points 610-617 represent individual pulse width and amplitude value pairs along the respective curves 601-604.

In one embodiment, processor 80 may receive a stimulation intensity value of "2", e.g., from a clinician via user interface 84. Processor 80 may then determine that the function represented by curve 602 corresponds to the received stimulation intensity value of "2" and defines the plurality of paired pulse width and amplitude values that correspond to the respective stimulation intensity value. Processor 80 may then select the paired pulse width and amplitude values represented by point 610 of curve 602. In this case, the values represented by point 610 may have the highest stimulation efficiency of all of the plurality of coupled values along curve 602 according to data in memory 82. Processor 80 may then generate stimulation parameters including the respective pulse width and amplitude values represented by point 610. IMD 19 may then deliver stimulation therapy according to the generated stimulation parameters.

Processor 80 may then receive a new stimulation intensity value of "3", e.g., from the clinician after the stimulation therapy generated and delivered according to the stimulation intensity value of "2". Processor 80 may then determine that the function represented by curve 603 corresponds to the received stimulation intensity value of "3" and defines the plurality of paired pulse width and amplitude values that correspond to the respective stimulation intensity value. In this case, processor 80 may then select the paired pulse width and amplitude values represented by point 611 of curve 603. In this case, the values represented by point 611 may have the highest stimulation efficiency of all of the plurality of coupled values along curve 603 according to data in memory 82. Processor 80 may then generate stimulation parameters that include the pulse width and amplitude values represented by point 611. IMD 19 may then deliver stimulation therapy according to the generated stimulation parameters. Furthermore, this process may be repeated for a received stimulation intensity value of "4" and point 612. As described, electrical stimulation therapy may be configured by utilizing one or more stimulation intensity values.

In another example that calculates stimulation efficiency in a manner different from the above example including points 610-612, processor 80 may receive a stimulation intensity value of "1", e.g., from a clinician via user interface 84. Processor 80 may then determine that the function represented by curve 601 corresponds to the received stimulation intensity value of "1" and defines the plurality of paired pulse width and amplitude values that correspond to the respective stimulation intensity value. Processor 80 may then select the paired pulse width and amplitude values represented by point 613 of curve 601. In this case, the values represented by point 613 may have the highest stimulation efficiency of all of the plurality of coupled values along curve 601 according to data in memory 82. Processor 80 may then generate stimulation parameters having the respective pulse width and amplitude values represented by point 613. IMD 19 may then deliver stimulation therapy according to the generated stimulation parameters.

Processor 80 may then receive a new stimulation intensity value of "2", e.g., from the clinician after the stimulation therapy generated and delivered according to the stimulation intensity value of "1". Processor 80 may then determine that the function represented by curve 602 corresponds to the received stimulation intensity value of "2" and defines the plurality of paired pulse width and amplitude values that correspond to the respective stimulation intensity value. In this case, point 617 may represent the paired pulse width and amplitude values with the highest stimulation efficiency. However, because point 617 is within area 610 that represents pulse width and amplitude values that have been excluded as potential stimulation values, e.g., because they have been determined to cause negative results in the patient, processor 80 may select the paired pulse width and amplitude values represented by point 614 of curve 602. In this case, the values represented by point 614 may have the highest stimulation efficiency of all of the non-excluded plurality of coupled values along curve 602 according to data in memory 82. Processor 80 may then generate stimulation parameters having the respective pulse width and amplitude values represented by point 614. IMD 19 may then deliver stimulation therapy according to the generated stimulation parameters. This process may be repeated for a received stimulation intensity values of "3" and "4", and points 615 and 616, respectively. As described, electrical stimulation therapy may be configured by utilizing one or more stimulation intensity values.

Figure 9:
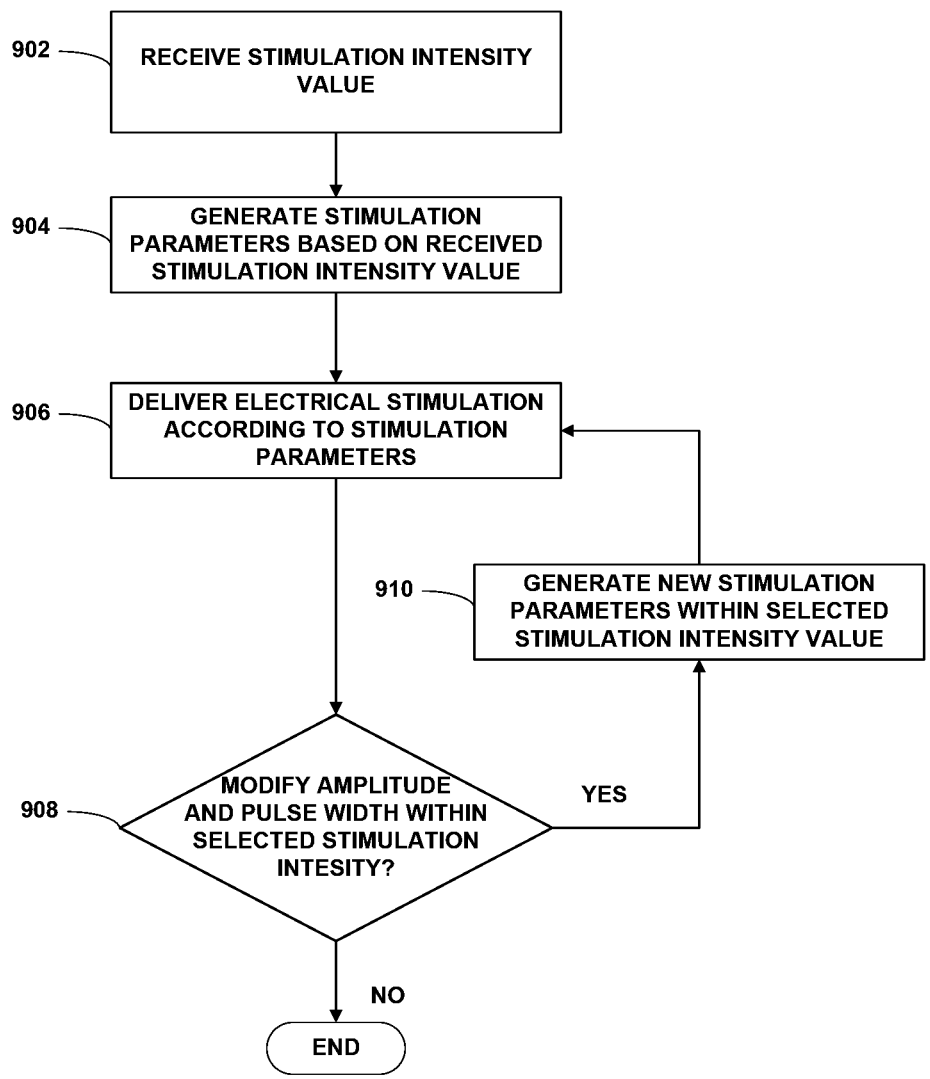
FIG. 9 is a flow diagram illustrating another example technique controlling delivery of electrical stimulation based on stimulation intensity values.

FIG. 9 is a flow diagram illustrating another example technique for controlling delivery of electrical stimulation based on stimulation intensity values. As indicated by FIG. 9, in some embodiments, multiple different pulse width and amplitude pairs of a single stimulation intensity value may be selected and used for delivery of stimulation. The technique for FIG. 9 may, for example, facilitate titration within one substantially equal intensity function, e.g., along a single substantially equal intensity curve. Titration within a single equal intensity function may facilitate identification of a pulse width and amplitude pair that is perceived as optimal. Further, titration within a single equal intensity function may be used, over time, to overcome neural accommodation, or to select a different pair if the relative efficiencies of the pairs defined by the single function change over time due to, for example, a changing voltage of power source 78 of IMD 20.

For example, processor 80 may receive a stimulation intensity value that corresponds to the equal intensity function represented by curve 402 (902) shown in FIG. 4. For the purposes of illustration, it may be assumed that the stimulation efficiency at point 406 is initially greater than points 404 and 408, and that stimulation efficiency at point 404 is initially greater than at point 408. Accordingly, processor 80 may first generate stimulation parameters by selecting a pulse width and amplitude value according to point 406 (904), and IMD 20 may deliver electrical stimulation according to the generated parameters (906). As indicated by FIG. 9, the stimulation may be modified (908) by generating new stimulation parameters according to a different individual coupled pulse width and amplitude values corresponding the same stimulation intensity value (910). For example, processor 80 may generate new stimulation parameters by selecting a pulse width and amplitude value according to point 404 (910), and IMD 20 may deliver electrical stimulation (906) according to the newly generated parameters (910). Substantially the same process may be followed to generate and deliver new stimulation parameters according to point 408.

As previously noted, the relative stimulation efficiency of pairs of pulse width and amplitude values may be influenced by one or more dynamic factors, such as, e.g., power source voltage level, power source age, and power source use. Accordingly, the most efficient pulse width and amplitude pair may change over time. In some embodiments, stimulation pulse width and amplitude pairs may be automatically or manually adjusted to maintain or maximize stimulation efficiency.

For example, system 10 may automatically perform a process similar to that illustrated in FIG. 9, to change the pulse width and amplitude pair of the electrical stimulation such that constant stimulation intensity is maintained while the efficiency of the stimulation is maximized or maintained in spite of the dynamic nature of stimulation efficiency. In some embodiments, processor 70 of IMD 20 may determine new relative stimulation efficiency values for the pulse width and amplitude pairs corresponding to the same stimulation intensity value on a periodic basis. For example, processor 70 may determine the new relative stimulation efficiency values based on changes to the voltage of its power source 78. Processor 70 may then generate new stimulation parameters by selecting a pulse width and amplitude value pair based on the new relative stimulation efficiency values, and control stimulation generator 74 to deliver electrical stimulation according to the newly generated parameters.

In some embodiments, processor 80 of programmer 19 may perform substantially the same function as described with respect to processor 70 of IMD 20, by, for example, periodically or opportunistically receiving information indicating a change in relative stimulation efficiency, e.g., receiving an updated power source voltage level from IMD 20. Processor 80 may control IMD 20 to deliver stimulation according to the new pulse width/amplitude pair As described herein, stimulation intensity values may correspond to a plurality of paired pulse width and amplitude values that activate a substantially equal volume of tissue when electrical stimulation having the pulse width and amplitude values is delivered. In general, systems utilizing such values may be preprogrammed with previously determined data that defines the plurality of paired pulse width and amplitude values corresponding to the stimulation intensity values.

In some examples, equal intensity functions that define the plurality of paired pulse width and amplitude values may be defined using one or more suitable estimation techniques. For example, an equal intensity function may be defined by the Weiss equation, the Lapicque equation, or combinations thereof. As another example, an equal intensity function may be based on a constant charge equation such that the integral of the current amplitude over the pulse width maintains a constant value. As another example, equal intensity functions may be defined based on relationships generated using electromagnetic/physiologic modeling techniques. In some cases, such estimation techniques may be modified on a patient by patient basis to calibrate the equal intensity functions to specific patients. For example, such modifications may be based on calibration stimulation delivered to the patient, previously sampled patients, animal studies, or modeling of the electrical stimulation.

In still another example, one or more equal intensity functions may be based on equal intensity curves generated by delivering and measuring the results of sufficient amount of various electrical pulses of different pulse width and amplitude pairs such that curves may be fit from the various pulse width and amplitude pair data points. While is some cases such a technique may be time consuming, the resulting equal intensity functions may be highly tailored to a given patient, especially to the electrode location and position of the lead in the specific patient. In some cases, equal intensity functions derived in this manner may be applied to other patient having similar circumstances.

In some examples, the plurality of paired pulse width and amplitude values corresponding to each individual stimulation intensity value may be determined based on previous electrical stimulation testing. Such testing may allow for the stimulation intensity values to be patient specific or nonspecific, e.g., the plurality of paired values may be determined during a preprogramming session for each patient or may be experimentally determined data that is not specific to the patient. In some examples, equal intensity functions may be estimated and then confirmed and/or modified using one or more suitable testing methods before being implemented into systems such as systems 10.

Figure 10:
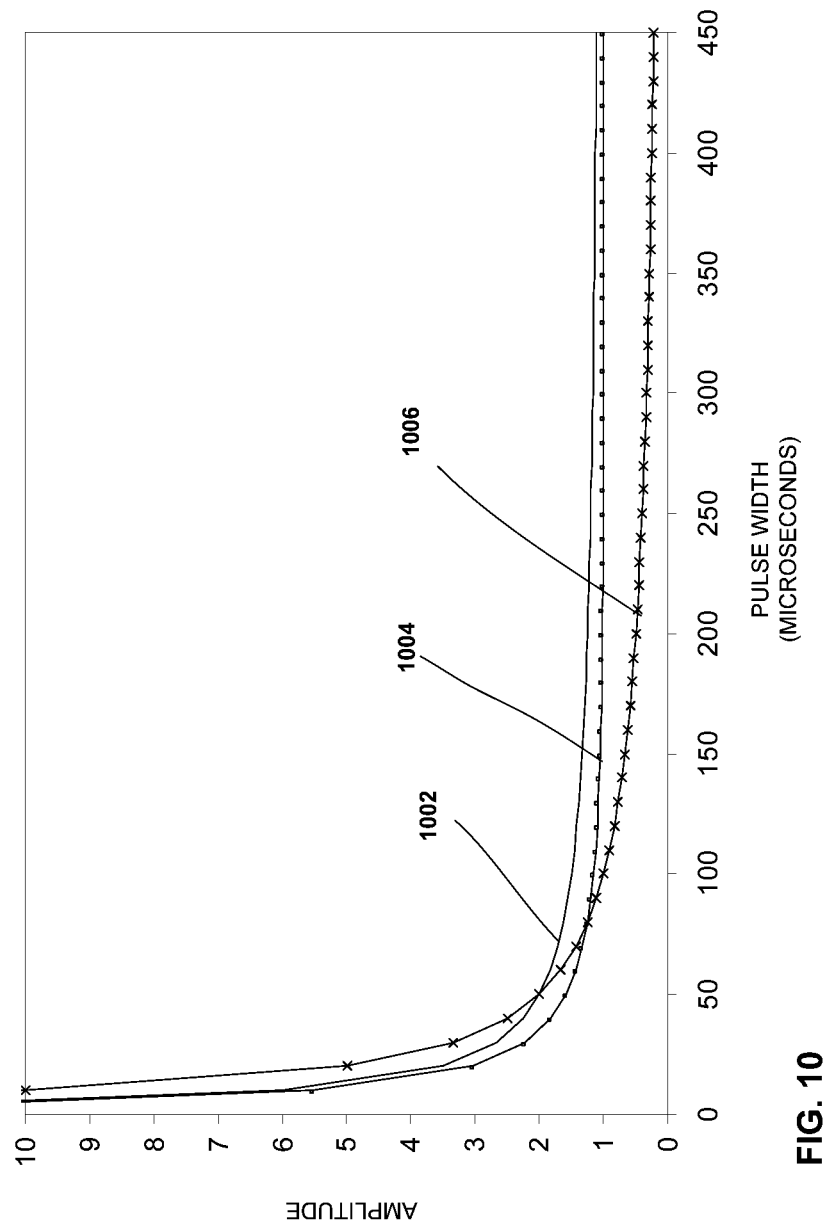
FIG. 10 is a plot of three example strength-duration curves generated via three different estimation techniques, respectively.

FIG. 10 is a plot of three example equal intensity curves generated via three different estimation techniques, respectively. Specifically, curve 1002 was generated via a form of the Weiss equation, curve 1004 was generated via a form of the Lapicque equation, and curve 1006 was generated via a constant charge equation. Accordingly, each of curves 1002, 1004, 1006 represents an estimation of a plurality of couple pulse width and amplitude values that activate a substantially equal volume of tissue with electrical stimulation according to the respective equation. In some embodiments, such equations may be used to define equal intensity functions corresponding to stimulation intensity values.

As described herein, each stimulation intensity value may correspond to a different plurality of paired pulse width and amplitude values such that each stimulation intensity value represents a different volume of tissue activated with electrical stimulation. In general, the relative stimulation intensity may be conveyed by any suitable means. In some embodiments, relative stimulation intensity may be conveyed to a user as unitless values, e.g., unitless numerals as used in FIG. 6. In such cases, the stimulation intensity numerals may be such that increases or decrease in the stimulation intensity value corresponds to an increase or decrease, respectively, of the stimulation intensity.

In other examples, the relative stimulation intensity may be conveyed to a user in terms of the percentage of maximum stimulation intensity. In some embodiments, the maximum stimulation intensity may be may be patient or IMD specific. For example, in embodiments in which the maximum stimulation intensity is patient specific, stimulation may be initially delivered to a patient to determine a maximum threshold that the stimulation can be delivered. The percent of stimulation intensity can then be calculated based on the stimulation intensity corresponding to the maximum threshold for determined for the patient. In other embodiments, the percent of stimulation intensity can be calculated based on the stimulation intensity corresponding to the maximum stimulation capabilities of the IMD, which can vary with respect to types of the IMD utilized.

In still other examples, standardized values may be used to convey relative stimulation intensity to a user. In some cases, standard values may be useful in relating the stimulation intensity of produced by a variety of IMDs. For example, a stimulation value of "50" in one type of IMD may be approximately the same relative stimulation intensity represented by a stimulation value of "50" of a different IMD. By using standardized values, stimulation intensity can be easily related among different types of IMDs with different stimulation capabilities.

In still other examples, the relative stimulation intensity may be conveyed to a user based on a minimum or perceivable stimulation threshold. In some embodiments, the minimum stimulation threshold may be the lowest stimulation intensity in which an effect of the stimulation is perceived by a patient. For example, stimulation may be initially delivered to a patient to determine the minimum stimulation intensity that the electrical stimulation elicits effects that are perceived by a patient. The determined minimum threshold stimulation intensity may then be used as a basis to convey the stimulation intensity of other electrical stimulation. In some embodiments, the stimulation intensity corresponding to the minimum threshold may be assigned a value, such as, e.g., a value of "0". Stimulation intensity that is greater than the minimum threshold may be assigned values that are relatively greater than the minimum value and stimulation that in less than the minimum threshold value may be assigned values that are relatively less than the minimum value. For example, stimulation intensity may be conveyed in terms of a percentage that reflects that percentage that the stimulation is greater than or less than the minimum threshold stimulation intensity.

In still other examples, relative stimulation intensity may be conveyed to a user based on the stimulation field produced by electrical stimulation according to the respective stimulation intensity. For example, relative stimulation value may be conveyed to a user based on the average radius of tissue or neuron activation in the stimulation field. As another example, relative stimulation value may be conveyed to a user based on the radius at which a given percentage of tissue activated is reached, or at which a threshold of activation is reached. In some cases, the stimulation field may vary depending on a number of factors, including the location of the lead delivering the stimulation, and the type of tissue to which the stimulation is delivered, e.g., in which the lead is implanted. Accordingly, stimulation having a same pulse width and amplitude values at may not necessarily produce the same stimulation field in all cases.

Figure 11:
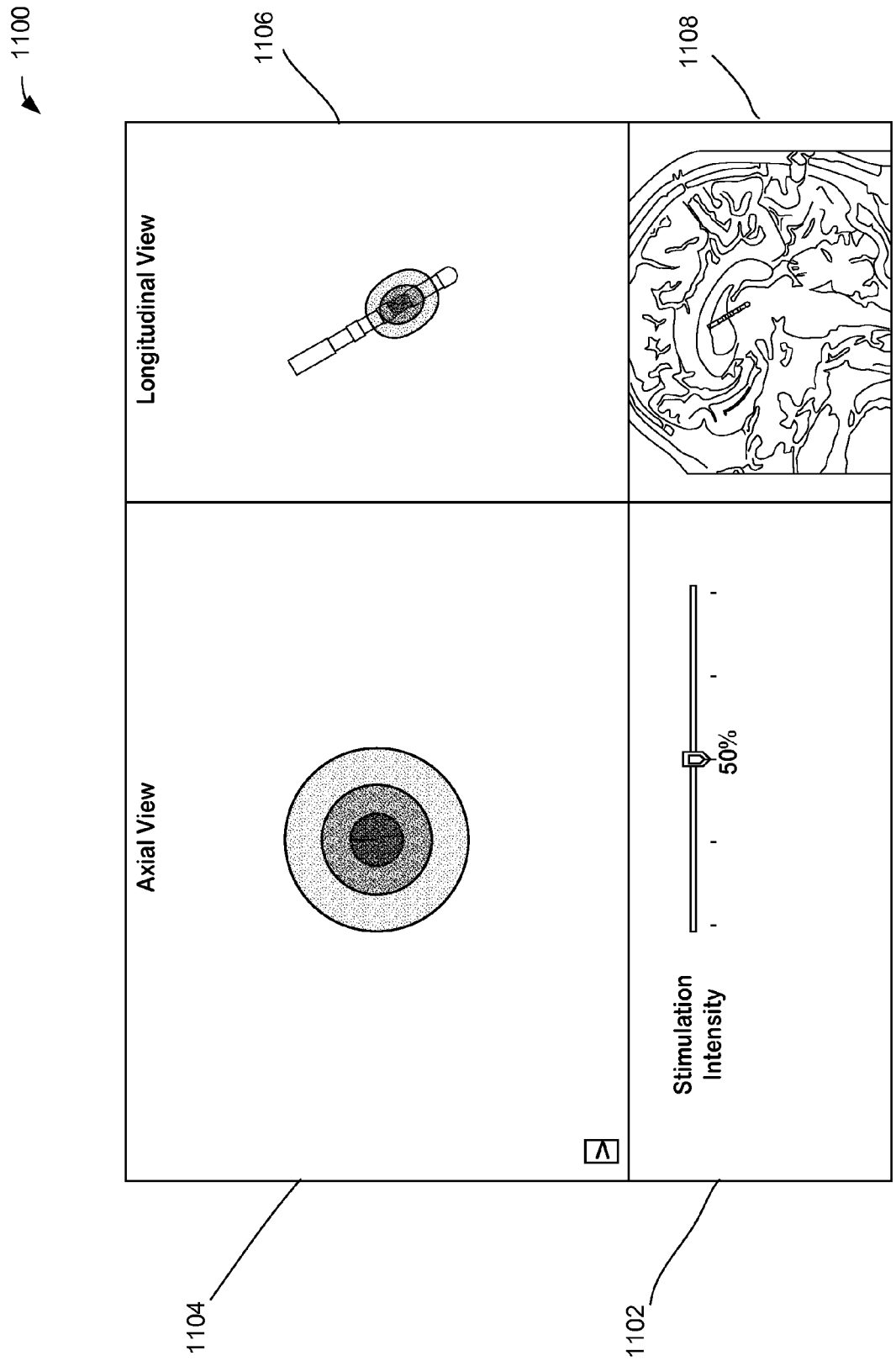
FIG. 11 is a diagram illustrating an example user interface for controlling delivery of stimulation based on stimulation intensity values.

FIG. 11 is a diagram illustrating an example user interface for selecting or modifying the stimulation intensity value. As shown, user interface 1100 includes first area 1102, second area 1104, third area 1106 and fourth area 1108. First area 1102 is includes a graphical representation of available stimulation intensity values that may be selected by a user to program electrical stimulation parameters. In this case, user interface 1100 presents the stimulation intensity values in terms of percentage of maximum stimulation intensity along a substantially horizontal slider-bar scale. One extreme of the slider-bar scale represents a stimulation intensity value of approximately 0%. The opposite extreme of the bar scale represents a stimulation intensity value of approximately 100%.

A user may interact with user interface 1100 to select a stimulation intensity value. As shown, a stimulation intensity value of 50% is selected. A user may interact with the bar scale to move the respective marker in either direction to modify the selected stimulation intensity value. The various positions on the slider-bar and associated percentage values may be associated with different stimulation intensity values.

In the embodiment shown, area 1108 includes a graphical representation of a patient's brain and also the location of a stimulation lead and associate electrodes. Also, areas 1104 and 1106 include graphical representation of the stimulation lead and associated electrodes, in addition to a graphical representation of the electrical stimulation field surrounding the electrode. Such a stimulation field may be estimated based on the stimulation parameters of the stimulation therapy including the pulse width and amplitude value, and the location of the electrode delivering the stimulation. As shown, a user may also interact with the representations of the stimulation field in areas 1104 and 1106 to select and/or modify the stimulation intensity value. For example, as previously explained, stimulation intensity may be conveyed based on the average radius of activation in the stimulation field. In this case, a user may interact with the stimulation field representation to modify the shape of the field. A change in the shape of the representation of the stimulation field may modify the stimulation intensity. In some cases, the bar scale in area 1102 may change according to the shape of the representation of the stimulation field, and vice versa.

In some examples, user interface 1100 may also include a graphical representation of additional parameters. For example, pulse frequency, battery life and/or stimulation efficiency may be displayed via user interface 1110 to a user. In some cases, the parameter values may be represented in real-time. For example, stimulation efficiency may be represented according to the selected stimulation intensity value. If the stimulation intensity value were to be change by a user, then the stimulation efficiency representation may change to represent the new stimulation intensity value. In this manner, a user may be informed in real-time the influence that the stimulation intensity value has on the stimulation efficiency. Additionally, the stimulation efficiency may be displayed after the parameters have been generated according to the selected stimulation intensity value but before the stimulation therapy has been delivered. As such, a user may be informed of the stimulation efficiency resulting from the stimulation intensity value without actually delivering the electrical stimulation therapy. In some cases, a user may decide not to deliver the electrical stimulation based on the stimulation efficiency estimated from the generated parameter values. Instead, the user may again modify the stimulation intensity value without delivering electrical stimulation according to the generated parameters.

Figure 12:
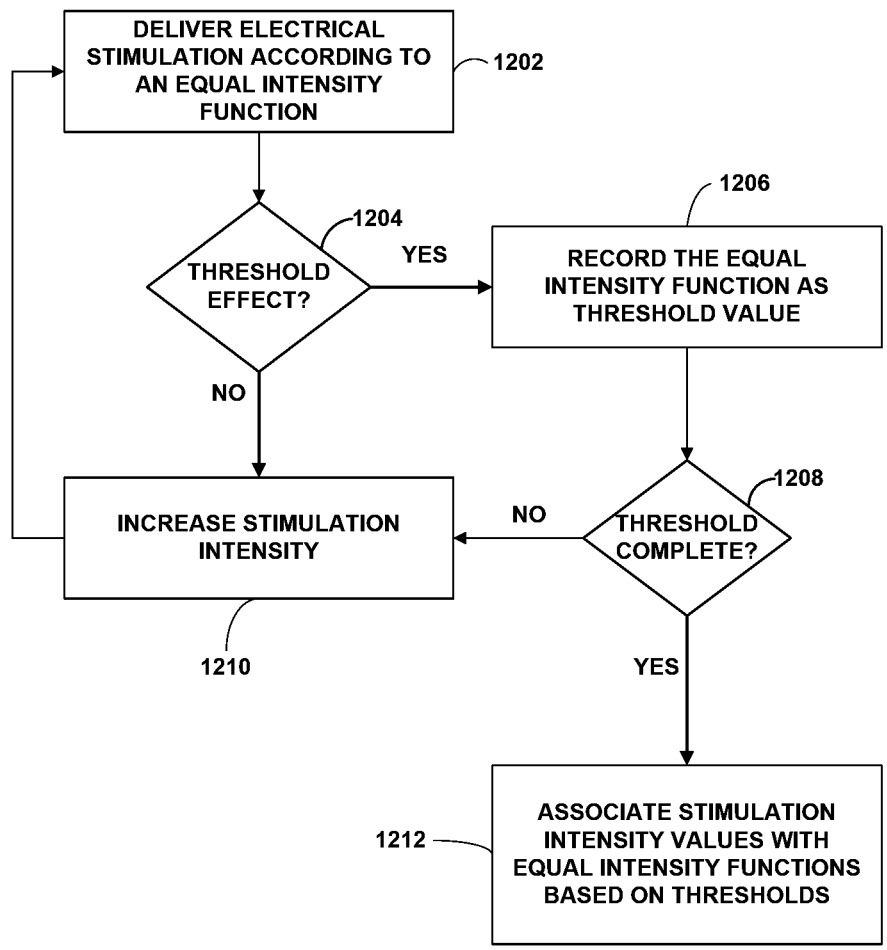
FIG. 12 is a flow diagram illustrating an example technique for determining associations between stimulation intensity values and equal intensity functions.

Irrespective of the technique used to allow a user to select a stimulation intensity value, the association between possible stimulation intensity values and respective equal intensity functions may, in some examples, vary between patients, and may be configurable for a particular patient. FIG. 12 illustrates an example technique for determining associations between stimulation intensity values and equal intensity functions, which may be patient-specific. As indicated in FIG. 12, electrical stimulation having a pulse width and amplitude value according to an equal intensity function may be delivered to a patient (1202). In the example illustrated by FIG. 12, the initial equal intensity function may generally provide for a relatively low stimulation intensity, e.g., based on stimulation delivered to one or more previous patients.

In some cases, the delivery of the electrical stimulation will elicit a threshold effect in the patient (1204). If the delivered electrical stimulation does not result in a threshold effect, the stimulation intensity of the electrical stimulation may be increased (1210) by delivering electrical stimulation according to an equal intensity function that corresponds to a relatively higher to stimulation intensity compared to the previously delivered stimulation (1202). As indicated by FIG. 12, such a process may be followed until the delivered electrical stimulation results in a threshold effect in the patient.

When the delivered electrical stimulation (1202) does elicit a threshold effect in a patient, the equal intensity function associated with the electrical stimulation may be recorded as a threshold value (1206). For example, a clinician may make a note via a programmer, e.g., by pressing a physical or graphical button, so that the respective equal intensity function may be stored in the memory of the programmer in addition to the threshold effect the equal intensity function elicited with electrical stimulation.

Once the equal intensity function has been recorded as a threshold value (1206), the process may continue by increasing the stimulation intensity of the electrical stimulation (1210) as described above such that additional equal intensity functions may be recorded as threshold values (1208). For example, as described in further detail below, the process may be used to record an equal intensity function corresponding to each of a perception threshold effect, therapeutic effect or usage level threshold effect, and a maximum stimulation or intolerable threshold effect. The thresholds may be associated with positive effects of stimulation and/or negative effects of stimulation.

Once all of the desired threshold values have been recorded (1208), stimulation intensity values may be associated with the equal intensity functions that were recorded as threshold values (1212). For example, a programmer may calibrate stimulation intensity values using the recorded threshold values as "data points" to define the instructions that will be used to determine which respective equal intensity function corresponds to a received stimulation intensity value. For example, the equal intensity function that was recorded as the eliciting the perception threshold may be associated with a relatively low stimulation intensity value. Similarly, the equal intensity function that was recorded as the eliciting the therapeutic effect threshold may be associated with a relatively medium stimulation intensity value. Further, the equal intensity function that was recorded as the eliciting the maximum stimulation or intolerable threshold may be associated with a relatively high stimulation intensity value. Accordingly, such a process may be used to provide for patient specific calibration of stimulation intensity values with respect to equal intensity functions.

The effect elicited on the patient by the electrical stimulation may be evaluated using any number of suitable techniques, e.g., evaluating the effect of the stimulation by monitoring physiological markers of the patient that may indicate an effect of the stimulation and/or evaluating the effect of the stimulation via patient feedback and clinician observation. Such techniques may be used to determine whether the delivered electrical stimulation (1204) has elicited a threshold effect (1204). As described above, an example of threshold effect may include a minimum or "perception threshold" in which effects, positive or negative, from the electrical stimulation are first perceived. For example, in SCS, a perceivable threshold effect may include the first onset of paresthesia experienced by a patient. As another example, in DBS, a perceivable threshold effect may include the first onset of an effect, which may be a clinical or positive effect (i.e., an effect that provides clinical benefit, such as, e.g., a reduction in tremor amplitude or in rigidity), or a negative side effect (i.e., an effect that is undesirable, such as, e.g., a muscle contraction). In some cases, a clinician may perform a standard test to identify the first onset of effects from electrical stimulation. A standard test may correspond to a one or more of standard metrics, e.g., with respect to Parkinson disease, one or more of the standard metric associated with the Unified Parkinson Disease Rating Scale (UPDRS).

In addition, another example threshold effect may relate to a therapeutic effect threshold in which effects elicited by the electrical stimulation achieve clinically relevant levels of disease state or symptom reduction, e.g. with respect to the above mentioned standard metric associated with the UPDRS. In a broader sense, such a threshold effect may be labeled a "usage threshold" effects in the sense that stimulation is above a minimum level and the effects can be tolerated even though there are some negative side effects. For example, in Subthalamic Nucleus (STN) DBS, such a threshold may relate to a level where a patient has good control of motor symptoms, but also experiences a tolerable level of hypophonia.

As also described above, another example threshold effect may relate to a maximum stimulation or intolerable threshold in which effects elicited by the electrical stimulation may include a relatively high number and/or level of negative side effects. In some cases, such effects may be intolerable, e.g., as judged subjectively by a patient or independently observed. Generally, any positive effect is clearly outweighed by the one or more negative effects elicited by the electrical stimulation at this threshold.

Although various examples have been described herein with respect to configuration of pulse width and amplitude values and without regard to other stimulation parameters, such as electrode combination and polarity, and stimulation frequency, one or more of these stimulation parameters may also be configured during a programming session according to this disclosure. In some cases, electrical stimulation frequency may be initially set at a default value based on one or more factors, such as electrode location and therapy type. In such situations, the stimulation intensity values may be used to generate pulse width and amplitude values while maintaining a constant stimulation frequency. However, a user may still also be able to modify the stimulation frequency and other parameters, e.g., using programmer 19, if desired.

Furthermore, although described herein with respect to examples in which programmer 19 selects paired pulse width and amplitude values based on a received intensity value, the disclosure is not so limited. In other examples, an IMD 20 may select pulse width and amplitude pairs using a substantially equal intensity function based on a stimulation intensity value, e.g., received from a user via programmer 19. IMD 20 may store substantially equal intensity functions within memory 72. Thus, any of the techniques described herein as being performed by programmer 19 and/or processor 80 of programmer 19 may additionally or alternatively be performed by IMD 20 and/or processor 70 of IMD 20

The disclosure is not limited to any configuration of system 10. For example, the techniques described herein may be implemented in any programmer or other computing device, any external or implantable medical device that delivers electrical stimulation, and with any lead set. Such systems may include cylindrical or paddle shaped leads including ring electrodes, or partial ring (i.e., segmented) electrodes. Such systems may be used for delivery of stimulation to any patient tissue, such nerves or other neural elements, or muscle tissue.

Additionally, although described primarily in the context of examples in which a pulse width and amplitude value pair is selected in response to user selection of a stimulation intensity value, the disclosure is not so limited. In other examples, a programmer, computing device, or stimulator (e.g., IMD) may automatically select the stimulation intensity values according to a program or sequence. For example, stimulation intensity values may be automatically selected during an automatic ramping up or down of stimulation intensity, e.g., at the beginning or end of a burst of pulses or when a program is first selected or unselected.

As described herein, the plurality of pulse width/amplitude pairs for one substantially equal intensity function may activate a substantially equal volume of tissue. The volume of tissue activated may depend on the type of tissue to which the stimulation is delivered, e.g., the fiber diameter of neural tissue. The actual shape of the tissue volume may also vary, and the tissue activated by pairs at any intensity may reflect a decreasing local percentage of activated tissue, e.g., neurons, at increasing distances from the one or more electrodes from which stimulation is delivered.

The invention claimed is:
1. A method comprising:
receiving a stimulation intensity value that corresponds to an equal intensity function;
determining a pulse width value and a pulse amplitude value based on the equal intensity function; and controlling delivery of electrical stimulation pulses with the determined pulse width value and amplitude value to a patient, wherein the equal intensity function defines a plurality of paired pulse width and amplitude values, each pair of the plurality of paired pulse width and amplitude values activating a substantially equal volume of tissue when electrical stimulation is delivered having the respective paired pulse width and amplitude values, wherein determining the pulse width value and the pulse amplitude value based on the equal intensity function comprises selecting one of the plurality of paired pulse width and amplitude values, and wherein at least one of the receiving, determining, and controlling is performed via one or more processors.

2. The method of claim 1, wherein selecting one of the plurality of paired pulse width and amplitude values comprises selecting the one of the plurality of paired pulse width and amplitude values based on at least one of relative efficiency of the paired pulse width and amplitude values, physiological guidelines, stimulation device limitations, stimulation device interlocks, or a type of tissue to be activated.

3. The method of claim 1, wherein selecting one of the plurality of paired pulse width and amplitude values comprises selecting the one of the plurality of paired pulse width and amplitude values based on relative efficiency of the paired pulse width and amplitude values, wherein relative efficiency of the paired pulse width and amplitude changes with respect to time, the method further comprising:

detecting a new relative efficiency of the plurality of paired pulse width and amplitude values, wherein selecting one of the plurality of paired pulse width and amplitude values further comprises selecting the one of the plurality of paired pulse width and amplitude values based on the new relative efficiency of the paired pulse width and amplitude values.

4. The method of claim 1, wherein selecting one of the plurality of paired pulse width and amplitude values comprises selecting the one of the plurality of paired pulse width and amplitude values based on relative power source consumption for delivery of stimulation pulses with the paired pulse width and amplitude values.

5. The method of claim 1, further comprising selecting the equal intensity function from among a plurality of equal intensity functions based on the received stimulation intensity value, wherein each of the equal intensity functions is associated with a respective one of a plurality of stimulation intensity values.

6. The method of claim 5, further comprising associating the stimulation intensity values with equal intensity functions based on patient-specific thresholds.

7. The method of claim 1, wherein receiving a stimulation intensity value comprises receiving input specifying the stimulation intensity value from a user.

8. The method of claim 7, further comprising displaying a graphical representation that corresponds to a plurality of stimulation intensity values to the user via a user interface to allow the user to select the stimulation intensity value.

9. The method of claim 8, wherein the graphical representation comprises a slider-bar.

10. The method of claim 8, wherein the graphical representation comprises a representation of a stimulation field.

11. The method of claim 1, wherein the stimulation intensity value comprises at least one of a unitless alphanumeric value, a percentage of a maximum stimulation intensity value, or a standardized value.

12. A system comprising:
a medical device configured to deliver electrical stimulation pulses to a patient; and
a processor configured to receive a stimulation intensity value that corresponds to an equal intensity function, determine a pulse width value and a pulse amplitude value based on the equal intensity function, and control the medical device to deliver electrical stimulation pulses with the determined pulse width value and amplitude value to a patient, wherein the equal intensity function defines a plurality of paired pulse width and amplitude values, each pair of the plurality of paired pulse width and amplitude values activating a substantially equal volume of tissue when electrical stimulation is delivered having the respective paired pulse width and amplitude values, and wherein the processor is configured to select one of the plurality of paired pulse width and amplitude values as the determined pulse width value and amplitude value.

13. The system of claim 12, wherein the processor is configured to select the one of the plurality of paired pulse width and amplitude values based on at least one of relative efficiency of the paired pulse width and amplitude values, physiological guidelines, limitations of the medical device, interlocks of the medical device, or a type of tissue to be activated.

14. The system of claim 12, wherein the processor is configured to select the one of the plurality of paired pulse width and amplitude values based on relative efficiency of the paired pulse width and amplitude values, wherein relative efficiency of the paired pulse width and amplitude values changes with respect to time, wherein the processor is configured to detect a new relative efficiency of the plurality of pulse width and amplitude values and selects the one of the plurality of paired pulse width and amplitude values based on the new relative efficiency of the paired pulse width and amplitude values.

15. The system of claim 12, wherein the processor is configured to select the one of the plurality of paired pulse width and amplitude values based on relative power source consumption for delivery of stimulation pulses with the paired pulse width and amplitude values.

16. The system of claim 12, wherein the processor is configured to select the equal intensity function from among a plurality of equal intensity functions based on the received stimulation intensity value, wherein each of the equal intensity functions is associated with a respective one of a plurality of stimulation intensity values.

17. The system of claim 16, wherein the processor is configured to associate the stimulation intensity values with equal intensity functions based on patient-specific thresholds.

18. The system of claim 12, further comprising a user interface, wherein the processor is configured to receive input specifying the stimulation intensity value from a user via the user interface.

19. The system of claim 18, wherein the processor is configured to display a graphical representation that corresponds to a plurality of stimulation intensity values to the user via the user interface for selection of the stimulation intensity value.

20. The system of claim 19, wherein the graphical representation comprises a slider-bar.

21. The system of claim 19, wherein the graphical representation comprises a representation of a stimulation field.

22. The system of claim 12, wherein the stimulation intensity value comprises at least one of a unitless alphanumeric value, a percentage of a maximum stimulation intensity value, or a standardized value.

23. The system of claim 12, wherein the medical device is implantable, and the processor comprises a processor of an external programmer for the medical device.

24. The system of claim 12, wherein the medical device is implantable, and the processor comprises a processor of the medical device.

25. A system comprising:
- means for receiving a stimulation intensity value that corresponds to an equal intensity function;
- means for determining a pulse width value and a pulse amplitude value based on the equal intensity function; and
- means for controlling delivery of electrical stimulation pulses with the determined pulse width value and amplitude value to a patient,
- wherein the equal intensity function defines a plurality of paired pulse width and amplitude values, each pair of the plurality of paired pulse width and amplitude values activating a substantially equal volume of tissue when electrical stimulation is delivered having the respective paired pulse width and amplitude values, and
- wherein the means for determining the pulse width value and the pulse amplitude value based on the equal intensity function comprises means for selecting one of the plurality of paired pulse width and amplitude values.

26. A non-transitory computer-readable storage medium comprising instructions to cause a programmable processor to:
- receive a stimulation intensity value that corresponds to an equal intensity function;
- determine a pulse width value and a pulse amplitude value based on the equal intensity function; and
- control delivery of electrical stimulation pulses with the determined pulse width value and amplitude value to a patient,
- wherein the equal intensity function defines a plurality of paired pulse width and amplitude values, each pair of the plurality of paired pulse width and amplitude values activating a substantially equal volume of tissue when electrical stimulation is delivered having the respective paired pulse width and amplitude values, and
- wherein the instructions to cause the processor to determine the pulse width value and the pulse amplitude value based on the equal intensity function comprise instructions to cause the processor to select one of the plurality of paired pulse width and amplitude values.

27. The non-transitory computer-readable storage medium of claim 26, wherein the instructions to cause the processor to select one of the plurality of paired pulse width and amplitude values comprise instructions to cause the processor to select the one of the plurality of paired pulse width and amplitude values based on relative efficiency of the paired pulse width and amplitude values.

28. The non-transitory computer-readable storage medium of claim 26, wherein the instructions to cause the processor to select one of the plurality of paired pulse width and amplitude values comprise instructions to cause the processor to select the one of the plurality of paired pulse width and amplitude values based on relative power source consumption for delivery of stimulation pulses with the paired pulse width and amplitude values.

* * * * *